United States Patent
Corkery et al.

(10) Patent No.: US 10,416,256 B2
(45) Date of Patent: Sep. 17, 2019

(54) METHOD AND APPARATUS FOR MEASURING PHYSICO-CHEMICAL PROPERTIES USING A NUCLEAR MAGNETIC RESONANCE SPECTROMETER

(71) Applicant: PepsiCo, Inc., Purchase, NY (US)

(72) Inventors: Robert Corkery, Stockholm (SE); Chris Dimelow, Leicestershire (GB); Sergey V. Dvinskikh, Vallentuna (SE); Adam Feiler, Hässelby (SE); Istvan Furo, Vallentuna (SE); Eapen George, Frisco, TX (US); Peter Given, Ridgefield, CT (US); Julie Anne Grover, Plano, TX (US); Pavel V. Yushmanov, Lidingö (SE)

(73) Assignee: PepsiCo, Inc., Purchase, NY (US)

( * ) Notice: Subject to any disclaimer, the term of this patent is extended or adjusted under 35 U.S.C. 154(b) by 308 days.

(21) Appl. No.: 15/591,204

(22) Filed: May 10, 2017

(65) Prior Publication Data
US 2017/0276750 A1 Sep. 28, 2017

Related U.S. Application Data

(62) Division of application No. 13/833,549, filed on Mar. 15, 2013, now Pat. No. 9,678,185.

(51) Int. Cl.
*G01R 33/44* (2006.01)
*G01N 24/08* (2006.01)

(52) U.S. Cl.
CPC .......... *G01R 33/448* (2013.01); *G01N 24/08* (2013.01)

(58) Field of Classification Search
CPC ................ G01R 33/448; G01N 24/08
See application file for complete search history.

(56) References Cited

U.S. PATENT DOCUMENTS 4,654,592 A * 3/1987 Zens .................. G01R 33/30
324/307
5,095,271 A 3/1992 Ohkawa
(Continued)

FOREIGN PATENT DOCUMENTS

EP 0544585 A1 3/1996
EP 0544585 B1 3/1996
(Continued)

OTHER PUBLICATIONS

Borgia, G. C., et al., "Uniform-Penalty Inversion of Multiexponential Decay Data," *Journal of Magnetic Resonance*, vol. 132: 65-77 (1998).

(Continued)

*Primary Examiner* — Dixomara Vargas
(74) *Attorney, Agent, or Firm* — Sterne, Kessler, Goldstein & Fox, P.L.L.C.

(57) ABSTRACT

Methods for measuring physico-chemical properties using a nuclear magnetic resonance spectrometer are disclosed, including methods to determine an initial amount of a substance, usually a liquid, contained inside a porous material and an initial amount of the substance, usually a liquid, present outside the porous material, methods to measure the release kinetics of a substance, such as a liquid, from a porous material, and methods for performing chemical reactions and other physico-chemical operations in situ inside a nuclear magnetic resonance probe after a sample is loaded into a nuclear magnetic resonance spectrometer. The apparatuses for performing these methods are also disclosed.

20 Claims, 13 Drawing Sheets

(56) References Cited

U.S. PATENT DOCUMENTS

| | | | |
|---|---|---|---|
| 5,258,712 A | 11/1993 | Hofmann et al. |
| 5,270,650 A | 12/1993 | Schenz et al. |
| 5,289,124 A | 2/1994 | Jerosch-Herold et al. |
| 5,302,897 A | 4/1994 | Tache et al. |
| 5,313,162 A | 5/1994 | De Graaf et al. |
| 5,321,358 A | 6/1994 | Mohr et al. |
| 5,387,865 A | 2/1995 | Jerosch-Herold et al. |
| 5,408,181 A | 4/1995 | Dechene et al. |
| 5,428,291 A | 6/1995 | Thomann et al. |
| 5,451,873 A | 9/1995 | Freedman et al. |
| 5,545,998 A | 8/1996 | Favre et al. |
| 5,596,275 A | 1/1997 | Dechene et al. |
| 5,650,722 A | 7/1997 | Smith et al. |
| 5,654,636 A | 8/1997 | Sweedler et al. |
| 5,696,448 A | 12/1997 | Coates et al. |
| 5,698,979 A | 12/1997 | Taicher et al. |
| 5,712,566 A | 1/1998 | Taicher et al. |
| 5,726,570 A | 3/1998 | Spraul et al. |
| 5,757,186 A | 5/1998 | Taicher et al. |
| 5,828,214 A | 10/1998 | Taicher et al. |
| 5,834,936 A | 11/1998 | Taicher et al. |
| 5,867,026 A | 2/1999 | Haner |
| 5,905,376 A | 5/1999 | Synderman et al. |
| 6,018,243 A | 1/2000 | Taicher et al. |
| 6,043,024 A | 3/2000 | Fesik et al. |
| 6,047,595 A | 4/2000 | Herron et al. |
| 6,051,973 A | 4/2000 | Prammer |
| 6,069,477 A | 5/2000 | Chen et al. |
| 6,072,314 A | 6/2000 | Oraby |
| 6,115,671 A | 9/2000 | Fordham et al. |
| 6,118,272 A | 9/2000 | Taicher et al. |
| 6,177,798 B1 | 1/2001 | Haner et al. |
| 6,229,308 B1 | 5/2001 | Freedman |
| 6,242,913 B1 | 6/2001 | Prammer |
| 6,291,996 B1 | 9/2001 | Glover et al. |
| 6,377,042 B1 | 4/2002 | Menger et al. |
| 6,380,737 B1 | 4/2002 | Myles |
| 6,396,267 B1 | 5/2002 | Riek et al. |
| 6,420,869 B1 | 7/2002 | DiFoggio |
| 6,437,565 B1 | 8/2002 | Early et al. |
| 6,452,389 B1 | 9/2002 | Edwards |
| 6,462,542 B1 | 10/2002 | Venkataramanan et al. |
| 6,522,136 B1 | 2/2003 | Hurlimann et al. |
| 6,570,382 B1 | 5/2003 | Hurlimann et al. |
| 6,597,171 B2 | 7/2003 | Hurlimann et al. |
| 6,646,438 B2 | 11/2003 | Kruspe et al. |
| 6,650,114 B2 | 11/2003 | Kruspe et al. |
| 6,674,282 B2 | 1/2004 | Pines et al. |
| 6,677,750 B2 | 1/2004 | Hennig et al. |
| 6,690,166 B2 | 2/2004 | Ni et al. |
| 6,755,246 B2 | 6/2004 | Chen et al. |
| 6,768,304 B2 | 7/2004 | Avizonis et al. |
| 6,774,635 B1 | 8/2004 | Gerald, II et al. |
| 6,794,864 B2 | 9/2004 | Mirotchnik et al. |
| 6,794,866 B2 | 9/2004 | Ferrage et al. |
| 6,822,454 B2 | 11/2004 | Peck et al. |
| 6,833,698 B2 | 12/2004 | Sun et al. |
| 6,838,880 B2 | 1/2005 | Hofmann et al. |
| 6,859,032 B2 | 2/2005 | Heaton et al. |
| 6,873,153 B2 | 3/2005 | Frydman |
| 6,897,652 B2 | 5/2005 | Appel et al. |
| 6,972,568 B2 | 12/2005 | Haner et al. |
| 7,009,393 B2 | 3/2006 | Cohen Addad et al. |
| 7,141,978 B2 | 11/2006 | Peck et al. |
| 7,145,340 B2 | 12/2006 | Rindlisbacher et al. |
| 7,221,158 B1 | 5/2007 | Ramakrishnan |
| 7,246,939 B1 | 7/2007 | Gultekin |
| 7,250,767 B2 | 7/2007 | Hofmann et al. |
| 7,271,588 B2 | 9/2007 | Frydman |
| 7,352,179 B2 * | 4/2008 | Chen ............ G01N 24/08 |
| | | 324/303 |
| 7,372,263 B2 | 5/2008 | Edwards |
| 7,397,240 B2 | 7/2008 | Fleury et al. |
| 7,397,241 B2 | 7/2008 | Gauthausen et al. |
| 7,456,630 B2 | 11/2008 | Gerald, II et al. |
| 7,459,907 B2 | 12/2008 | Ganesan |
| 7,492,157 B2 | 2/2009 | Kitagawa et al. |
| 7,501,236 B1 | 3/2009 | Knox et al. |
| 7,511,488 B2 | 3/2009 | Romero et al. |
| 7,518,371 B2 * | 4/2009 | Spraul ............ G01R 33/307 |
| | | 324/321 |
| 7,550,971 B2 | 6/2009 | Carpenter et al. |
| 7,576,538 B2 | 8/2009 | Meersmann et al. |
| 7,612,563 B2 | 11/2009 | Massin et al. |
| 7,622,919 B2 | 11/2009 | Song et al. |
| 7,626,386 B2 | 12/2009 | Bodenhausen et al. |
| 7,683,613 B2 | 3/2010 | Freedman et al. |
| 7,705,592 B2 | 4/2010 | Hursan |
| 7,719,273 B2 | 5/2010 | Kitagawa et al. |
| 7,737,691 B2 | 6/2010 | Gerald, II et al. |
| 7,753,119 B2 | 7/2010 | Chen et al. |
| 7,764,064 B2 | 7/2010 | Reiss et al. |
| 7,804,297 B2 | 9/2010 | Romero |
| 7,839,144 B2 | 11/2010 | Jebutu |
| 7,852,074 B2 | 12/2010 | Edwards |
| 7,852,077 B2 | 12/2010 | Song et al. |
| 7,894,891 B2 | 2/2011 | Song et al. |
| 7,898,256 B2 | 3/2011 | Kitagawa et al. |
| 7,940,043 B2 | 5/2011 | Gao et al. |
| 7,940,045 B2 | 5/2011 | Carpenter et al. |
| 7,965,078 B2 | 6/2011 | Cheng et al. |
| 8,004,279 B2 | 8/2011 | Kruspe et al. |
| 8,013,601 B2 | 9/2011 | Cheng et al. |
| 8,044,662 B2 | 10/2011 | Fransson et al. |
| 8,134,365 B2 | 3/2012 | Carpenter et al. |
| 8,421,458 B2 * | 4/2013 | Lowery, Jr. ............ G01R 33/30 |
| | | 324/307 |
| 9,018,950 B2 | 4/2015 | Li et al. |
| 9,678,185 B2 * | 6/2017 | Corkery ............ G01N 24/08 |
| 2004/0233423 A1 * | 11/2004 | Nakayama ......... G01N 21/0303 |
| | | 356/246 |
| 2005/0287527 A1 | 12/2005 | Ni et al. |
| 2006/0116828 A1 * | 6/2006 | Chen .................. G01N 24/08 |
| | | 702/22 |
| 2006/0164088 A1 * | 7/2006 | Hawkes ............ G01R 33/3415 |
| | | 324/321 |
| 2007/0224692 A1 | 9/2007 | Agar et al. |
| 2008/0036457 A1 | 2/2008 | Thern et al. |
| 2009/0000880 A1 | 1/2009 | Noguchi et al. |
| 2009/0256562 A1 | 10/2009 | Gao et al. |
| 2010/0090698 A1 | 4/2010 | Blumich et al. |
| 2010/0120174 A1 | 5/2010 | Josephson et al. |
| 2010/0227755 A1 | 9/2010 | Saito |
| 2010/0301858 A1 * | 12/2010 | Lowery, Jr. ............ G01R 33/30 |
| | | 324/309 |
| 2011/0025324 A1 | 2/2011 | Fransson et al. |
| 2011/0091987 A1 | 4/2011 | Weissleder et al. |
| 2011/0105886 A1 | 5/2011 | Song et al. |
| 2011/0137567 A1 | 6/2011 | Li et al. |
| 2011/0181278 A1 | 7/2011 | Chen et al. |
| 2011/0181279 A1 | 7/2011 | Srnka et al. |
| 2011/0204892 A1 | 8/2011 | Li et al. |
| 2011/0223297 A1 | 9/2011 | Corkery et al. |
| 2011/0234220 A1 | 9/2011 | Mitchell et al. |
| 2011/0275985 A1 | 11/2011 | Lowery, Jr. et al. |
| 2011/0285396 A1 | 11/2011 | Hofmann et al. |
| 2011/0316534 A1 | 12/2011 | Kamar et al. |
| 2012/0049844 A1 | 3/2012 | Leveridge et al. |
| 2012/0062226 A1 | 3/2012 | Pielak et al. |
| 2012/0092013 A1 | 4/2012 | Marquez et al. |
| 2012/0286779 A1 | 11/2012 | Walsh et al. |
| 2013/0316327 A1 * | 11/2013 | Lowery, Jr. ............ G01R 33/30 |
| | | 435/5 |
| 2014/0266194 A1 * | 9/2014 | Corkery ............ G01N 24/08 |
| | | 324/309 |

FOREIGN PATENT DOCUMENTS

| | | |
|---|---|---|
| EP | 2341372 A1 | 7/2011 |
| WO | WO 2007/109772 A2 | 9/2007 |
| WO | WO 2009/045551 A1 | 4/2009 |
| WO | WO 2009/045670 A1 | 4/2009 |
| WO | WO 2009/067361 A1 | 5/2009 |

(56) References Cited

FOREIGN PATENT DOCUMENTS

| WO | WO 2009/097507 A2 | 8/2009 |
|---|---|---|
| WO | WO 2009/097510 A2 | 8/2009 |
| WO | WO 2009/102846 A2 | 8/2009 |
| WO | WO 2010/002479 A1 | 1/2010 |
| WO | WO 2010/060631 A1 | 6/2010 |
| WO | WO 2011/071796 A2 | 6/2011 |
| WO | WO 2011/094275 A2 | 8/2011 |
| WO | WO 2011/154370 A1 | 12/2011 |

OTHER PUBLICATIONS

Borgia, G. C., et al., "Uniform-Penalty Inversion of Multiexponential Decay Data: II. Data Spacing, $T_2$ Data, Systematic Data Errors, and Diagnostics," *Journal of Magnetic Resonance*, vol. 147: 273-285 (2000).

Yushmanov, P. V., et al., "A rapid-mixing design for conventional NMR probes," *Journal of Magnetic Resonance*, vol. 175: 264-270 (2005).

International Search Report for International Application No. PCT/US2014/024549, United States Patent and Trademark Office, United States, dated Jul. 9, 2014, 2 pages.

Written Opinion for International Application No. PCT/US2014/024549, United States Patent and Trademark Office, United States, dated Jul. 9, 2014, 6 pages.

International Preliminary Report on Patentability for International Application No. PCT/US2014/024549, The International Bureau of WIPO, Switzerland, dated Sep. 15, 2015, 7 pages.

\* cited by examiner

METHOD AND APPARATUS FOR MEASURING PHYSICO-CHEMICAL PROPERTIES USING A NUCLEAR MAGNETIC RESONANCE SPECTROMETER

FIELD OF THE INVENTION

This invention relates to measuring physico-chemical properties of materials using nuclear magnetic resonance spectroscopy ("NMR"). In particular, some aspects of the invention relate to a method of measuring and interpreting a sample's NMR transverse relaxation and an apparatus performing such a method. The apparatus and method may include components for performing chemical reactions and transport phenomena in situ inside a NMR probe, and therefore other aspects of the invention relate to an apparatus and method for performing in situ reactions for NMR spectroscopy.

BACKGROUND

NMR spectroscopy is known as one of the most important diagnostic tools available to scientists and engineers across a wide range of fields. Therefore, this disclosure assumes familiarity with the primary aspects of NMR spectroscopy and experiments, and will only focus on the aspects most relevant to the applications described herein rather than providing an exhaustive summary. To the extent further explanation may be helpful, review of J. Keeler, *Understanding NMR Spectroscopy*, Wiley, 2006; B. Cowan, *Nuclear Magnetic Resonance and Relaxation*, Cambridge University Press, 1997; J. Kowalewski and L. Maier, *Nuclear Spin Relaxation in Liquids*, Taylor & Francis, 2006; or similar references can help elucidate the foundational principles of the field.

Numerous atoms with odd atomic numbers and/or odd atomic mass numbers such as Hydrogen have nonzero nuclear spin and therefore possess a nuclear magnetic moment. An atom such as Hydrogen with a spin quantum number of $I=\frac{1}{2}$ has two possible nuclear spin states when placed in a magnetic field as its nuclear magnetic moment orients relative to the field. In one spin state the nuclear magnetic moment orients parallel to the direction of the applied magnetic field while the other orients directly against the direction of the applied field. Under Boltzmann's law and in thermal equilibrium, there is a slight preference for that alignment that has a lower energy, meaning for a sample comprising many Hydrogen nuclei (or nuclei with similar spin properties), the overall spin population of the sample favors this state. Therefore, the overall magnetic moment of a sample is typically characterized as showing the sample has a net nuclear magnetization along the direction of the z-axis, where this axis is defined by the direction of the applied magnetic field.

When the sample is irradiated with a radiofrequency ("RF") pulse, generating a second magnetic field, one may probe the properties of the sample by reorienting the overall nuclear magnetization vector of the sample and manipulating the relative populations of the overall spins. Often, a RF pulse will be applied to a sample such that its magnetization is moved from the z-axis into a coherent vector in the x-y (transverse) plane. Once the RF pulse is finished, however, the created nuclear magnetization in the transverse plane decays to zero in a process called transverse relaxation while the magnetization along the z-axis relaxes back to its value attained in thermal equilibrium in a process called longitudinal relaxation. The measured decay of signal in the transverse plane provides the transverse, relaxation time typically denoted as $T_2$.

NMR experiments may be performed on a wide variety of molecules. Transverse relaxation times for molecules, however, are sensitive to molecular motions. Therefore, experiments directed to samples where some amount of the sample material has a greater degree of molecular motion compared to some other amount of the same material that is constrained or contained in some way, such as within a porous material, will observe differences in the transverse relaxation times between the constrained and unconstrained material. In these systems, quantifying the relative amounts of free, out-of-pore material and constrained in-pore material is far from straightforward. This is especially true when the material is a liquid due to factors including the distribution of liquid properties, the pore size variance and distribution, and differences in the size of liquid droplets. Therefore, typical multiexpoential fits of the experimental transverse relaxation decays are not suitable as they provide strongly model dependent answers.

Certain types of NMR experiments may also relate to measuring the kinetics of a system, such as a chemical reaction or a chemical transport phenomenon. Due to the inherent time (in the order of 10 seconds or longer) needed to load an NMR sample into the spectrometer, however, conventional techniques preclude measuring the immediate kinetics or characteristics of a system or transformation after the sample is prepared, as the chemical reaction or transformation begins to proceed before the sample is loaded in the spectrometer.

To alleviate these inefficiencies, it may be desirable to utilize a method and apparatus that accurately allows the differentiation of constrained and unconstrained materials. It may also be desirable to utilize a method and apparatus that allows initiation of a chemical reaction or other transformation only after the sample is loaded into the NMR spectrometer and ready for measurement.

The invention provides NMR methods and apparatuses that, amongst other features and advantages, address these objectives. Certain embodiments of the invention provide a method and apparatus for determining an initial amount of a substance such as a liquid contained inside a porous material and an initial amount of the substance such as a liquid present outside the porous material using a nuclear magnetic resonance spectrometer. Certain other embodiments provide a method for measuring the release kinetics of a substance such as a liquid from a porous material using a nuclear magnetic resonance spectrometer. Still other embodiments provide an apparatus and method for performing chemical reactions or other transformations in situ inside a nuclear magnetic resonance probe after a sample is loaded into a nuclear magnetic resonance spectrometer. These and other objects, features and advantages of the invention or of certain embodiments of the invention will be apparent to those skilled in the art from the following disclosure and description of exemplary embodiments.

SUMMARY

In accordance with one aspect of the invention, a method for measuring physico-chemical properties of a sample, such as the sample's release kinetics properties, using a nuclear magnetic resonance spectrometer is disclosed, the method comprising placing the sample inside a nuclear magnetic resonance probe, wherein the sample comprises a porous material and a substance such as a liquid that is at least partially contained inside the porous material, applying a first radiofrequency pulse or pulse sequence to the sample, measuring a first transverse relaxation decay of the sample and performing an inverse Laplace transformation on the first measured transverse relaxation decay to determine an initial amount of the substance such as the liquid contained inside the porous material and an initial amount of the substance such as the liquid present outside the porous material.

In certain of these embodiments, the sample comprises a contacting solution and the method further comprises exposing the porous material and the substance such as the liquid to the contacting solution, waiting a predetermined time period after the first measurement of the sample's transverse relaxation, applying at least one subsequent radiofrequency pulse or pulse sequence to the sample, measuring at least one subsequent transverse relaxation decay of the sample, performing an inverse Laplace transformation on the at least one subsequent transverse relaxation decay to determine at least one subsequent amount of the substance such as the liquid contained inside the porous material and at least one subsequent amount of the substance such as the liquid present outside the porous material and comparing the initial amounts of the substance such as the liquid inside and outside the porous material to the at least one subsequent amounts of the substance such as the liquid inside and outside the porous material.

In certain embodiments, the pulse or pulse sequence is a Carr-Purcell-Meiboom-Gill (CPMG) radiofrequency pulse sequence. In others, the contacting solution comprises water, a buffer, an organic solvent, an inorganic solvent, a model saliva solution, a model blood solution, a model gastric acid solution, or a combination thereof. In yet other embodiments, the contacting solution is substantially or entirely Deuterated. In yet other embodiments, the substance of interest contains a unique NMR nucleus such as but not exclusively $^{31}P$, $^{19}F$, $^{23}Na$ that is not present in the contacting solution. In all these embodiments, the NMR signal that is unique to the substance of interest is detected while the NMR signal of the contacting solution is not detected, or is only detected in small amounts. In still other embodiments, the substance such as the liquid comprises an edible organic compound, an edible oil, a flavorant, a sweetener, a pharmaceutical compound, a medicament, an ink, or a combination thereof.

In some embodiments, the porous material and the substance such as a liquid are exposed to the contacting solution in situ inside the probe after the probe is loaded into the nuclear magnetic resonance spectrometer such that the probe is ready for measurement of the sample's transverse relaxation. In other embodiments, the porous material and the substance such as a liquid are stored inside a first container, the contacting solution is stored inside a second container, the first container is contained inside the second container and separates the porous material and the substance such as a liquid from the contacting solution, and the method further comprises exposing the porous material and the substance such as a liquid to the contacting solution by removing the first container, forcing the porous material and the substance such as a liquid out of the first container, or a combination thereof. In certain embodiments, the method further comprises applying an electric current to a conductor material to produce a Lorentz force, where the Lorentz force acts upon the conductor material such that the conductor material initiates or performs the removing of the first container, the forcing of the porous material and the substance such as a liquid, or a combination thereof. In other embodiments the conductor material is a solenoid coil and the electric current produces a Lorentzian torque that causes the solenoid coil to rotate. In still other embodiments, the porous material is an edible grain or particle, while in others it specifically comprises Silicon dioxide particles.

In accordance with another aspect of the invention, an apparatus for measuring physico-chemical properties, such as the diffusion characteristics of a sample using nuclear magnetic resonance is disclosed, the apparatus comprising a nuclear magnetic resonance probe suitable for containing a sample, where the sample comprises a porous material and a substance such as a liquid that is at least partially contained inside the porous material, and one or more non-transitory computer readable media storing computer readable instructions that, when executed by a computer processor, cause the apparatus to perform applying a first radiofrequency pulse or pulse sequence to the sample, measuring a first transverse relaxation decay of the sample and performing an inverse Laplace transformation using the computer processor on the first transverse relaxation decay to determine an initial amount of the substance such as a liquid contained inside the porous material and an initial amount of the substance such as a liquid outside the porous material.

In some embodiments, the sample further comprises a contacting solution and the computer readable instructions, when executed, cause the apparatus to perform exposing the porous material and the substance such as a liquid to the contacting solution, waiting a predetermined time period after the measurement of the sample's first transverse relaxation, applying at least one subsequent radiofrequency pulse or pulse sequence to the sample, measuring at least one subsequent transverse relaxation decay of the sample. performing an inverse Laplace transformation on the at least one subsequent transverse relaxation decay to determine at least one subsequent amount of the substance such as a liquid contained inside the porous material and at least one subsequent amount of the substance such as a liquid outside the porous material and comparing the initial amounts of substance such as a liquid inside and outside the porous material to the at least one subsequent amounts of substance such as a liquid inside and outside the porous material. In yet other embodiments the porous material and the substance such as a liquid are stored inside a first container, a contacting solution is stored inside a second container, the first container is contained inside the second container and separates the porous material and the substance such as a liquid from the contacting solution and the first container is connected to an exposure mechanism. In other embodiments the exposure mechanism comprises an electrical source and a conductor material electrically connected to the electrical source, where the conductor material is directly or indirectly connected to the first container.

In accordance with another aspect of the invention, a method for measuring the release kinetics of a substance such as a liquid from a porous material using a nuclear magnetic resonance spectrometer is disclosed, the method comprising placing a sample inside a nuclear magnetic resonance probe, wherein the sample comprises a porous material, a substance such as a liquid that is at least partially contained inside the porous material, and a contacting solution, wherein the contacting solution is separated from the porous material and the substance such as a liquid. The method in accordance with the aspect of this invention further comprises exposing the porous material and the substance such as a liquid to the solution, applying a first radiofrequency pulse or pulse sequence to the sample and beginning a measurement of a first transverse relaxation decay of the sample, waiting a predetermined time period after the measurement of the sample's first transverse relaxation, applying at least one subsequent radiofrequency pulse or pulse sequence to the sample, measuring at least one subsequent transverse relaxation decay of the sample, performing an inverse Laplace transformation on the first measured transverse relaxation decay to determine an initial amount of the substance such as a liquid contained inside the porous material and an initial amount of the substance such as a liquid present in the contacting solution outside the porous material, performing an inverse Laplace transformation on the at least one subsequent transverse relaxation decay to determine at least one subsequent amount of the substance such as a liquid contained inside the porous material and at least one subsequent amount of the substance such as a liquid in the containing solution outside the porous material and comparing the initial amounts of substance such as a liquid inside the porous material and the contacting solution to the at least one subsequent amounts of substance such as a liquid inside the porous material and the contacting solution to determine the release kinetics of the substance such as a liquid into the contacting solution without use of a multi-exponential fit.

In certain embodiments, the porous material is an edible grain or particle. In yet others, the contacting solution comprises water, a buffer, an organic solvent, an inorganic solvent, a model saliva solution, a model blood solution, a model gastric acid solution, or a combination thereof. In still others, the substance such as a liquid comprises an edible organic compound, an edible oil, a flavorant, a sweetener, a pharmaceutical compound, an ink, or a combination thereof.

In accordance with another aspect of the invention, an apparatus for performing chemical reactions or other physico-chemical transformations in situ inside a nuclear magnetic resonance probe is disclosed, the apparatus comprising a sample container, a separator that separates at least a first sample component of a sample from at least a second sample component of the sample inside the sample container, an exposure mechanism connected to the separator that can expose at least the first sample component to at least the second sample component inside the sample container, wherein the exposure mechanism can be selectively activated to expose at least the first sample component to at least the second sample component inside the sample container at any time after the components are loaded, including when the sample is loaded in the nuclear magnetic resonance probe such that it is ready for the application of a radiofrequency pulse or pulse sequence by the nuclear magnetic resonance probe, and wherein the sample components, when the sample container is loaded into the nuclear magnetic resonance spectrometer, are positioned within a sample space encircled by a probe coil of the nuclear magnetic resonance probe.

In certain embodiments the exposure mechanism is configured to lift the separator from the sample, force at least the first sample component into contact with the second sample component, or a combination thereof when activated. In others the exposure mechanism further comprises an electrical source and a conductor material electrically connected to the electrical source, where the conductor material is directly or indirectly connected to the separator. In yet others the conductor material is mounted such that it will move or rotate in a particular way due to a Lorentz force when an electrical current is supplied by the electrical source to the conductor material and the conductor material is in the presence of a magnetic field. In certain other embodiments the conductor material is a solenoid coil and the electric current produces a Lorentzian torque that causes the solenoid coil to rotate. In still others the rotation of the solenoid coil lifts up the separator while mechanically forcing at least the first sample component into contact with at least the second sample component.

In other embodiments, the separator is a tube having a first diameter, the sample container is a tube having a second diameter, the second diameter being larger than the first diameter. In yet other embodiments, the separator is hermetically sealed to the bottom of the sample container. In certain other embodiments, the exposure mechanism further comprises a shaft capable of moving at least the first sample component along a longitudinal axis of the apparatus such that it drives at least the first sample component into at least the second sample component. In yet other embodiments, all components of the holder, separator, sample container and exposure mechanism that are in contact with the sample or come into close proximity to the sample are made of materials that are substantially or completely free of hydrogen.

In accordance with another aspect of the invention, a method for performing chemical reactions or other physico-chemical transformations in situ inside a nuclear magnetic resonance probe is disclosed, the method comprising loading a sample into a sample container, wherein a separator separates at least a first sample component of the sample from at least a second sample component of the sample inside the sample container, placing the sample into a nuclear magnetic resonance spectrometer, wherein the sample components, once the sample is placed into the nuclear magnetic resonance spectrometer, are positioned within a sample space encircled by a probe coil of a nuclear magnetic resonance probe, and exposing at least the first sample component to at least the second sample component inside the sample container when the sample is ready for the application of a radiofrequency pulse or pulse sequence by a nuclear magnetic resonance probe.

In certain embodiments, the first sample component is exposed to at least the second sample component by lifting the separator from the sample, forcing at least the first sample component into contact with the second sample component, or a combination thereof. In other embodiments, the method further comprises applying an electrical current to a conductor material such that the conductor material moves or rotates in a particular way due to a Lorentz force. In yet other embodiments, the conductor material is a solenoid coil and the electric current produces a Lorentzian torque that causes the solenoid coil to rotate. In still others, the rotation of the solenoid coil lifts up the separator while mechanically forcing at least the first sample component into contact with at least the second sample component. In certain others, the separator is a tube having a first diameter, the sample container is a tube having a second diameter, the second diameter being larger than the first diameter. In yet other embodiments, the method further comprises forcing at least the first sample component into contact with at least the second sample component using a shaft moving along a longitudinal axis of the apparatus.

In accordance with still another aspect of the invention, an apparatus for performing chemical reactions or other physico-chemical operations or transformations in situ inside a nuclear magnetic resonance probe is disclosed, the apparatus comprising a sample container, a separator that separates at least a first sample component of a sample from at least a second sample component of the sample inside the sample container, wherein at least one sample component comprises a solid material and wherein the sample components, when the sample container is loaded into the nuclear magnetic resonance spectrometer, are positioned within a sample space encircled by a probe coil of the nuclear magnetic resonance probe, and one or more non-transitory computer readable media storing computer readable instructions that, when executed by a computer processor, cause the apparatus to perform selectively activating the exposure mechanism to expose at least the first sample component to at least the second sample component inside the sample container, applying a first radiofrequency pulse or pulse sequence to the sample; and measuring the sample's magnetic resonance signals.

In certain embodiments, the exposure mechanism is configured to lift the separator from the sample, force at least the first sample component into contact with the second sample component, or a combination thereof when activated. In yet others the exposure mechanism further comprises an electrical source and a conductor material electrically connected to the electrical source, where the conductor material is directly or indirectly connected to the separator and the conductor material is mounted such that it will move or rotate in a particular way due to a Lorentz force when an electrical current is supplied by the electrical source to the conductor material and the conductor material is in the presence of a magnetic field.

BRIEF DESCRIPTION OF THE DRAWINGS

Exemplary embodiments of the disclosure will now be described by way of example only and with reference to the accompanying drawings, in which.

DETAILED DESCRIPTION OF EMBODIMENTS

Figure 1:
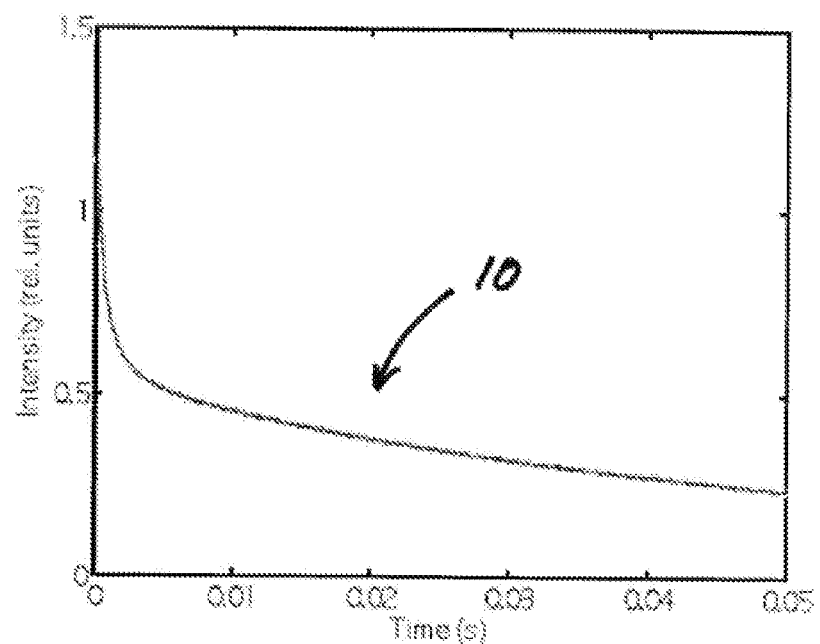
FIG. 1 provides a representative transverse relaxation signal decay measured by a CPMG pulse sequence, for sunflower oil loaded in SP104 particles.

The embodiments, apparatuses and methods described herein provide methods for determining an initial amount of a substance such as a liquid contained inside a porous material and an initial amount of the substance such as a liquid present outside the porous material, measuring the release kinetics of a substance such as a liquid from a porous material, for performing chemical reactions or other physico-chemical transformations or operations in situ inside a nuclear magnetic resonance probe after a sample is loaded into a nuclear magnetic resonance spectrometer, and the apparatuses for performing these methods. These and other aspects, features and advantages of the invention or of certain embodiments of the invention will be further understood by those skilled in the art from the following description of exemplary embodiments. It is to be understood that other embodiments may be utilized and structural and functional modifications may be made.

As noted above, relaxation times are sensitive to molecular motions. In particular, the transverse relaxation of a material is sensitive to molecular motions in the millisecond to nanosecond time interval. These relatively slower motions can shorten the transverse relaxation time of a material. In a porous material, interactions or collisions between a liquid and the wall of the porous material or basic geographic confinement due to the pore size can slow molecular motions and therefore lower the transverse relaxation time of the liquid due to these processes. In addition, the magnetic field within a random porous material is typically very inhomogeneous because the magnetic susceptibility, or magnetization of a material in response to an applied magnetic field, is different for the pore filling liquid and the porous material matrix. This inhomogeneity also promotes transverse relaxation by destroying coherence in the transverse plane since different nuclei experience different magnetic fields which, moreover, may fluctuate as molecules diffuse within the porous network.

In certain embodiments of the invention, a method is provided to determine an initial amount of a substance such as a liquid contained inside a porous material and an initial amount of the substance such as a liquid present outside of the porous material by measuring and taking advantage of the differences in transverse relaxation times for the in-pore and out-of-pore material (liquid). In some of these embodiments, a contacting solution is also present in or associated with the sample, where the porous material and the substance such as a liquid may or may not be in contact with the contacting solution at the time of initial measurement. In certain embodiments, the porous material and the substance such as a liquid are not in contact with the contacting solution for one or more measurements and subsequently are in contact with the contacting solution for one or more measurements. The transverse relaxation decay may be measured for any NMR active nuclei, including but not limited to $^1H$, $^2H$, $^{13}C$, $^{19}F$, $^{23}Na$, and $^{31}P$.

In some of these embodiments, the porous material and contacting solution (if present) preferably are substantially or entirely free of the nuclear species being measured. For example, in some embodiments measuring the $^1$H signal of the substance such as a liquid, the porous material and contacting solution (if present) are inorganic materials, Deuterated materials, or a combination thereof. In other examples, in some embodiments measuring $^{19}$F or $^{31}$P signal of the liquid, the porous material and contacting solution (if present) are substantially or entirely free of $^{19}$F, or $^{31}$P, respectively. In certain other embodiments, however, this is not necessary as the transverse relaxation of the relevant species in the solid porous material is very short and can be directly differentiated from the liquid's transverse relaxation or does not interfere with measurement of the liquid's transverse relaxation. As a representative example, the $^1$H transverse relaxation time of rigid cellulose or other rigid polymers is often on the time scale of 10 to 20 microseconds and therefore can be easily separated from the $^1$H transverse relaxation decay of liquids. In certain embodiments of the invention, consequently, the porous material can comprise the nuclear species of interest provided it does not interfere with the measurement of the sample's signal under experimental conditions.

The porous material, the substance of interest such as a liquid and the contacting solution may be a wide variety of materials. In some embodiments, the substance such as a liquid is constituted by a single material, while in others the substance such as a liquid is a solvent, carrier fluid, or liquid media that contains at least one other solid, liquid, or gas material. In certain embodiments, the liquid comprises an edible organic compound, an edible oil, a flavorant, a sweetener, a pharmaceutical compound, a medicament, an ink, or a combination thereof. In still other embodiments, the liquid comprises a medium chain triglyceride, propylene glycol, glycerine, citrus or other natural flavorants, or sunflower oil. The porous material can be organic or inorganic.

Additional flavorants that are suitable in certain embodiments of the invention are described in more detail in U.S. patent application Ser. No. 12/723,100, entitled "Anti-Caking Agent for Flavored Products," which is hereby incorporated by reference in its entirety. In some of these embodiments, the liquid comprises a dissolved or suspended solid or liquid flavorant that includes extracts, essential oils, essences, distillates, resins, balsams, juices, sugars, botanical extracts, flavor, fragrance, or flavoring constituents derived from a spice, fruit or fruit juice, vegetable or vegetable juice, edible yeast, herb, bark, bud, root, leaf or similar plant material, meat, seafood, poultry, eggs, dairy products, or fermentation products.

In certain embodiments, the substance such as a medicament comprises vitamins, minerals, nutritional supplements, diuretics, antivirals, antibiotics, anti-inflammatories, antitussives, or a combination thereof. In yet other embodiments, the substance such as edible oils comprises olive oil, peanut oil, safflower oil, corn oil, sunflower oil, cottonseed oils, canola, flax seed oil, coconut oil, palm oil, fish oil, avocado oil, walnut oil, macadamia nut oil, sesame seed oil, grapeseed oil, soybean oil, almond oil, orange oil, lime oil, black pepper oil, nutmeg oil, basil oil, rosemary oil, clove oil, grapefruit oil, fennel oil, coriander oil, bergamot oil, cinnamon oil, lemon oil, peppermint oil, garlic oil, thyme oil, marjoram oil, lemongrass oil, ginger oil, cardamom oil, or a combination thereof.

In certain embodiments, the porous material comprises one of more solid materials to form a porous matrix. In some embodiments, the porous material has substantially uniform pore diameters or pore sizes. In other embodiments, the porous material comprises pores with varying sizes or diameters, and in yet others the porous material comprises relatively defined proportions of pores with a first size or diameter and pores with at least one other size or diameter. Use of the invention is not constrained by the nature of the porous material as long as the substance of interest within the pores exhibits transverse relaxation times significantly different from that outside the pores. In some embodiments, the pore sizes or diameters can take any value in between 1 and 1000 nanometers, while in others they are substantially equal to or smaller than 500 nanometers. In others the pore sizes or diameters are substantially equal to or smaller than 250, 100 or 50 nanometers. In yet other embodiments, the pore sizes or diameters are between approximately 0.1 and 1 micrometers, 0.1 and 0.5 micrometers, and 0.5 and 1 micrometers, while in others there are between approximately 5 and 20 nanometers, 25 and 50 nanometers, and 50 and 100 nanometers.

In some embodiments, the porous material is a grain or particle. In other embodiments, the porous material is edible. In some of these embodiments, the porous material comprises Silicon dioxide, Magnesium oxide, Calcium oxide, Titanium dioxide, Zinc oxide, or a combination thereof. In still other embodiments, the porous material comprises mesoporous silica particles such as SP104 (mesoporous silica particles from a P104 pluronic template), SCTAB (mesoporous silica particles from a cetyl trimethylammonium bromide template), or a combination thereof. Certain other embodiments of the porous material are also described in U.S. patent application Ser. No. 12/723,100, referenced above and incorporated in its entirety by reference to this disclosure.

In still other embodiments, the porous material comprises an acrylate, a plastic, a polymer or a combination thereof. In yet other embodiments, the porous material comprises a hydrogel, a soluble polymer, a biodegradable polymer, a natural gum, or a combination thereof. In certain other embodiments, the porous material comprises polyethylene, polyvinyl chloride, ethyl cellulose, acrylate polymers, polyhydroxyethyl methylacrylate, cross-linked polyvinyl alcohol, cross-linked polyvinyl pyrrolidone, polyacrylamide, polyethylene glycol, polyvinyl alcohol, polyvinyl pyrrolidone, hydroxypropyl methyl cellulose, polylactic acid, polyglycolic acid, polycaprolactone, a polyanhydride, a polyorthoester, polyethylene vinyl acetate, polydimethyl siloxane, polyether urethane, polyvinyl chloride, cellulose acetate, ethyl cellulose, polycarbophil, sodium carboxymethyl cellulose, polyacrylic acid, tragacanth, methyl cellulose, pectin, xanthan gum, guar gum, karaya gum, or a combination thereof.

In some embodiments, the contacting solution comprises water, a buffer, an organic solvent, an inorganic solvent, a model saliva solution, a model blood solution, a model gastric acid solution, or a combination thereof. In certain of these embodiments, the contacting solution is substantially or entirely Deuterated so as to not interfere with the $^1$H NMR measurement. In some of these embodiments, the solution is "heavy" water where Deuterium has substantially or entirely replaced Hydrogen in the water. In certain other embodiments, the solution comprises Deuterated acetone, Deuterated methanol, Deuterated dimethyl sulfoxide, Deuterated chloroform, Carbon tetrachloride, or Carbon disulphide or a combination thereof. In various other embodiments, the contacting solution comprises an inorganic material. In yet other embodiments, the buffer is a mucin buffer, an electrolyte buffer, or a combination thereof.

In some embodiments an RF pulse or pulse sequences are used to measure the transverse relaxation decay of a sample loaded in the NMR spectrometer. In certain embodiments, a 90 pulse is used to orient the sample's magnetization into the transverse plane. In other embodiments, a pulse sequence is used to refocus the magnetization in the transverse plane. In certain embodiments, a Hahn spin echo sequence or related sequence is used. In still other embodiments, a Carr-Purcell pulse sequence, Carr-Purcell-Meiboom-Gill ("CPMG") pulse sequence, or a related pulse sequence is used. The CPMG sequence and other pulse sequences aid the accurate measurement of the transverse relaxation decay by at least correcting for magnetic field inhomogeneities and/or pulse accuracy errors. Another advantage of the CPMG sequence or similar sequences, however, is that they are relatively quick, often on the scale of approximately 100 milliseconds, which permits good temporal resolution in kinetic experiments.

Certain aspects of the invention relate to determining the amount of a substance, usually a liquid, inside and outside a porous material using the sample's transverse relaxation.

Figure 2:
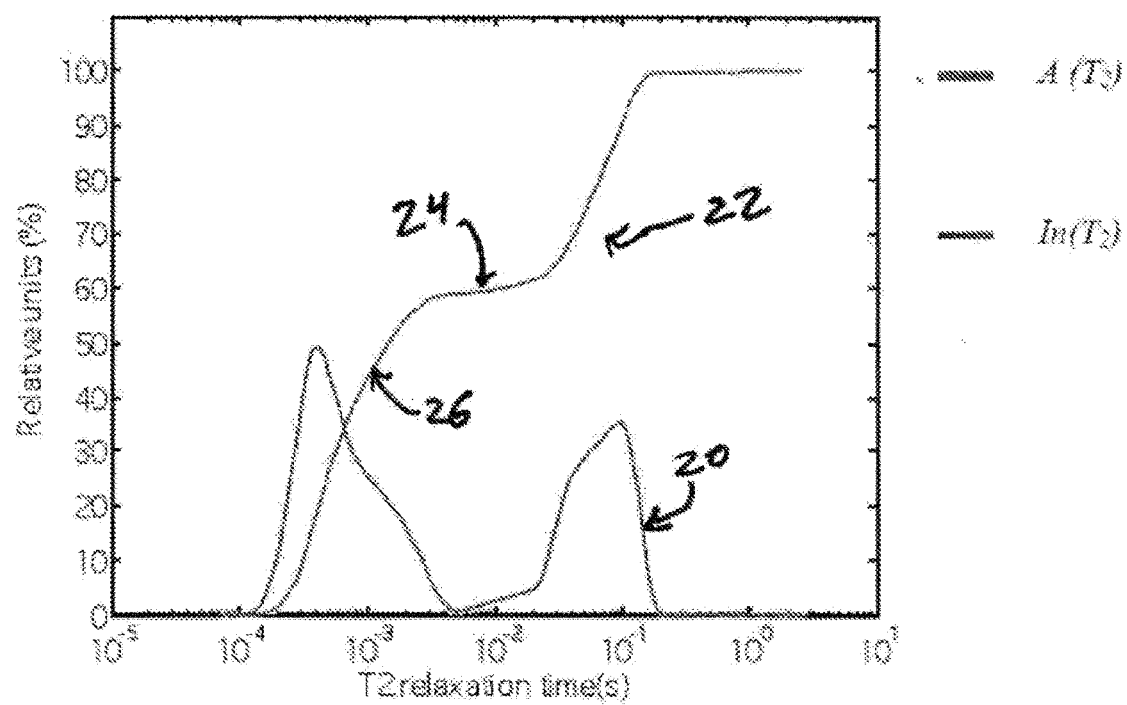
FIG. 2 provides the result of an inverse Laplace transformation of the transverse relaxation decay data of the embodiment from FIG. 1.

FIG. 1 provides an exemplary embodiment's transverse relaxation curve 10. In this exemplary embodiment, a Bruker Avance 500 NMR spectrometer measured a sample of sunflower oil (liquid) loaded into SP104 mesoporous silica particles using a CPMG sequence having 250 microsecond pulse spacing. Here only the early part of the decay is shown to emphasize the fast initial decay of signal in the transverse plane after the pulse sequence. Transverse relaxation curve 10 clearly shows the multi-exponential behavior of the signal decay. The fast initial decay is attributed to the shorter transverse relaxation time of sunflower oil contained in the pores of the SP104 for the reasons discussed above, while the longer tail is attributed to out-of-pore oil. As noted earlier, however, it is difficult to properly apportion the relative amount of oil in each of these states and multi-exponential fits are strongly model dependent. General multi-exponential behavior provides a transverse relaxation decay that can be written as:

$$I(t) = \int_{T_2 min}^{T_2 max} A(T_2) \cdot \exp\left(-\frac{t}{T_2}\right) dT_2$$

where I(t) is the exponential decay (as in FIG. 1) and $A(T_2)$ is the weighing factor for a particular $T_2$, e.g. the $T_2$ relaxation time for the in-pore or out-of-pore oil in this embodiment. The weighing factor is proportional to the fraction of molecules in a particular environment characterized by a given $T_2$ value, e.g. the ratio of in-pore to out-of-pore oil in this embodiment. Formally, I(t) is the Laplace transform of the weighing factor. Since determination of the weighing factor is needed to define the relative proportions of molecules, the transform needs to be inverted. Inverting Laplace transformation is mathematically ill-posed, however (in contrast to Fourier transformation) and the weighing factor therefore is determined by numerical inverse Laplace transformation. In certain embodiments, since the inverse Laplace transformation is ill-posed and is numerical, it is therefore not unique and for that reason two or more different numerical inverse Laplace transformation algorithms are used for control purposes, including UPEN (See Borgia G C, Brown R J S, Fantazzini P., *Uniform-penalty Inversion of Multiexponential Decay Data*, 132 J. MAGNETIC RESONANCE, 65-77 (1998); Borgia G C, Brown R J S, Fantazzini P., *Uniform-penalty Inversion of Multiexponential Decay Data II. Data Spacing, T2 Data, Systematic Data Errors, and Diagnostic*, 147 J. MAGNETIC RESONANCE, 273-85 (2000)), and RILT (see Regularized Inverse Laplace Transform function available for Matlab Central) (all of which are incorporated herein by reference in their entirety). The result of the inverse Laplace transformation can also be expressed as:

$$In(T_2) = \int_{T_2 min}^{T_2 max} A(T_2) dT_2$$

where the integral $In(T_2)$ is normalized to 100% at the maximum detected $T_2$ value. FIG. 2 provides the result of the inverse Laplace transformation of the embodiment data from FIG. 1, wherein curve 20 provides the representation of the weighing factor $A(T_2)$ and curve 22 the representation of $In(T_2)$. The internal plateau 24 visible in curve 22 separates the in-pore and out-of-pore oil components. The in-pore oil is responsible for the initial upward slope 26 of curve 22 in the range of approximately 10 milliseconds or less. Thus, the fraction of in-pore material is estimated by the plateau height 24 on the relative units scale of the y axis.

Use of various embodiments of this method can allow a skilled artisan to discern several physico-chemical properties of a sample. In certain embodiments, a sample comprising a porous material and a liquid that is at least partially contained in the porous material is placed in a spectrometer, a pulse or pulse sequence is applied, the transverse relaxation decay is measured, and an inverse Laplace transformation is performed. By examining the data as described above, the amount of in-pore liquid and out-of-pore liquid can be determined. In certain embodiments, this establishes the capacity of a particular porous substance for a particular liquid, the efficiency of a pore loading processes, or both. For example, in certain embodiments the efficiency of filling pores via capillary action is determined.

In certain other embodiments, the sample may further comprise a contacting solution and the porous material and liquid are exposed to the contacting solution. In some embodiments, this exposure is before any application of a RF pulse or pulse sequence and subsequent measurement, while in others one or more RF pulses or pulse sequences are applied and subsequent measurements are taken before the exposure to the solution. Various embodiments include any order of these steps. In some embodiments, the initial state or states of a sample is clearly ascertained and its exposure to the contacting solution is then measured and compared to the initial state or states. In other embodiments, only the state or states of the sample after exposure to the contacting solution are measured. In embodiments where multiple pulses or pulse sequences are applied in a relatively short time period and multiple measurements are taken, such as in kinetic experiments, a predetermined time period separates the transverse relaxation decay measurements to ensure the magnetization of the sample completely returns to its original strength along the z-axis. As is known in the art, the optimal amount of time should be determined experimentally for each sample. Certain embodiments of the method use two second delay between transverse relaxation decay measurements.

In certain other aspects of the invention, the long term steady state or long term kinetics of the sample are measured. In some of these embodiments, an initial transverse relaxation decay is measured before the porous material and liquid are exposed to the contacting solution and one or more subsequent transverse relaxations are measured after the exposure. In certain embodiments, the one or more subsequent transverse relaxation decay measurements are taken minutes after exposure to the contacting solution, in others hours later, and in still others days later. In yet other embodiments, the measurements are repeated on regular intervals of these time periods (e.g. approximately every 30 minutes). The number of repeated measurement may be whatever number is needed to acquire a sufficiently clear transverse relaxation decay depending on the nuclear species of interest and subject to any desired kinetic intervals. In some embodiments, 1, 2, 4, 8 or 16 transverse relaxations are measured. In others, at least 32, 64, 128, 256, or 512 are measured to determine the amount of in-pore and out-of-pore oil.

In some embodiments, at least one subsequent transverse relaxation decay is measured after approximately 15 minutes, 1 hour, 6 hours, 12 hours, 24 hours, 48 hours, or a combination thereof. In these embodiments, performing an inverse Laplace transformation on the initial and at least one subsequent transverse relaxations and comparing the results provides the long term steady state characteristics and/or long term kinetics of the sample. Among other benefits, a skilled artisan can use these embodiments to examine the delivery of a medicament or a pharmaceutical compound in the gastric environment or the blood stream.

Certain other aspects of the invention relate to providing a method for measuring the release kinetics of a liquid from inside a porous material. In some embodiments, the method comprises placing a sample in a nuclear magnetic resonance probe, where the sample comprises a porous material a liquid that is at least partially contained or imbibed inside the porous material, and a contacting solution, wherein the contacting solution is separated from the porous material and the at least partially imbibed liquid. The porous material and liquid then are exposed to the contacting solution, a RF pulse or pulse sequence is applied and a transverse relaxation decay is measured. As noted above, the exposure to the contacting solution may occur before or after the first RF pulse/pulse sequence and subsequent measurement. After waiting a predetermined time period, one or more subsequent pulse/pulse sequences are applied and relaxations measured. In some embodiments, the measurements begin almost immediately after exposure of the porous material and liquid to the solution and are repeated at relatively short intervals. Conversion of the measurements by inverse Laplace transformation therefore provides the short term kinetic data for the release kinetics of the liquid from the porous material into the contacting solution.

The measurement of the sample's transverse relaxation decay can begin almost immediately after the exposure of the porous material and liquid to the contacting solution. In certain embodiments, some dead time is required due to any mechanical disturbances such as fast internal convection in the sample caused by the exposure. In some embodiments, the dead time is less than about 100 milliseconds after the exposure is initiated. In certain other embodiments, especially those where the liquid is released relatively quickly, effective measurements can only begin approximately 500 milliseconds later as rapid convective flow of the liquid obliterates the signal at shorter times. As discussed above, some delay period between measurements is required for accurate results. In certain embodiments of the method, a two second delay is used, which for some samples allows accurate measurements of strong signal by allowing the magnetization to fully resume its initial state, yet is frequent enough to provide insightful kinetic data. In other embodiments and systems, however, any delay that provides accurate results and some insight into the short term kinetics of the system may be used, including delays of approximately 0.5, 1, 1.5, 2.5, 3, 5, 10, 30, 60, 120, or 180 seconds.

Any desired number of transverse relaxation decays may be measured. In some embodiments, 512 relaxation measurements are taken to accurately capture the relevant kinetic period, while other embodiments use approximately 8, 16, 32, 64, 128, 256, 612, 1024, or 2048 measurements. The appropriate number is in part dependent on the properties of the particular sample and/or the desired applications of the sample. Similarly, the recording time for each transverse relaxation decay can vary across different embodiments. In some embodiments, the relaxation is recorded over approximately 500 milliseconds, while in others the recording time is approximately 100, 175, 250 or 750 milliseconds. In still others the recording time is approximately 1 second, 1.25, 1.5, 1.75 or 2 seconds.

Figure 3:
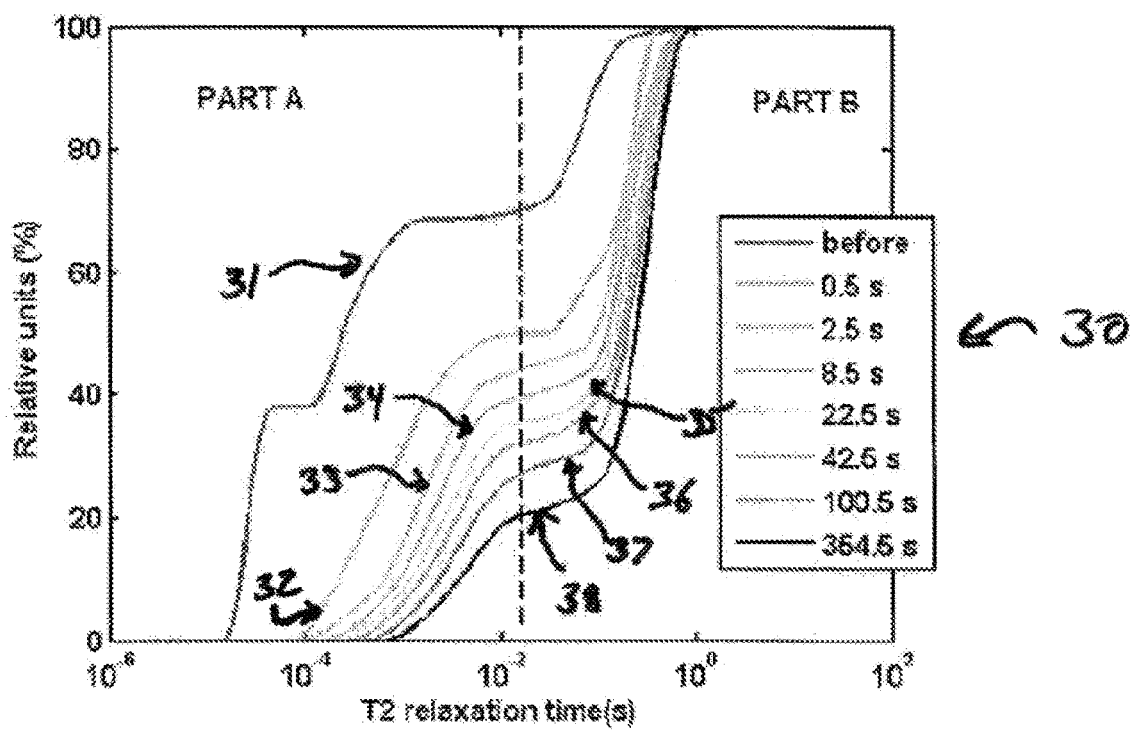
FIG. 3 provides the results of an inverse Laplace transformation of the transverse relaxation decay data of medium chain triglyceride oil loaded into SCTAB particles, where measurements were taken of the sample's initial transverse relaxation decay and then at a series of representative time periods after exposure to a mucin buffer solution.

In FIG. 3, plot 30 reflects the transverse relaxation data after the inverse Laplace transformation for an exemplary embodiment of the release kinetics determination method. In this exemplary embodiment, porous SCTAB particles were loaded with medium chain triglyceride oil and exposed to a mucin buffer contacting solution. In FIG. 3, curve 31 reflects the initial state of the sample before the porous material and oil were exposed to the buffer. As before the approximate plateau height of the curve provides the relative proportions of in-pore and out of pore-material, where here approximately 70% of the oil is inside the pores of the SCTAB. Curve 32 reflects the transverse relaxation measurement taken 500 milliseconds after exposure to the buffer solution, where approximately 50% of the oil remains inside the pores of the SCTAB material. Curve 33 reflects the transverse relaxation measurement taken 2 seconds later, or 2.5 seconds after exposure, and curves 34-38 reflect representative measurements taken 8.5, 22.5, 42.5, 100.5 and 354.5 seconds after exposure, respectively.

Figure 4:
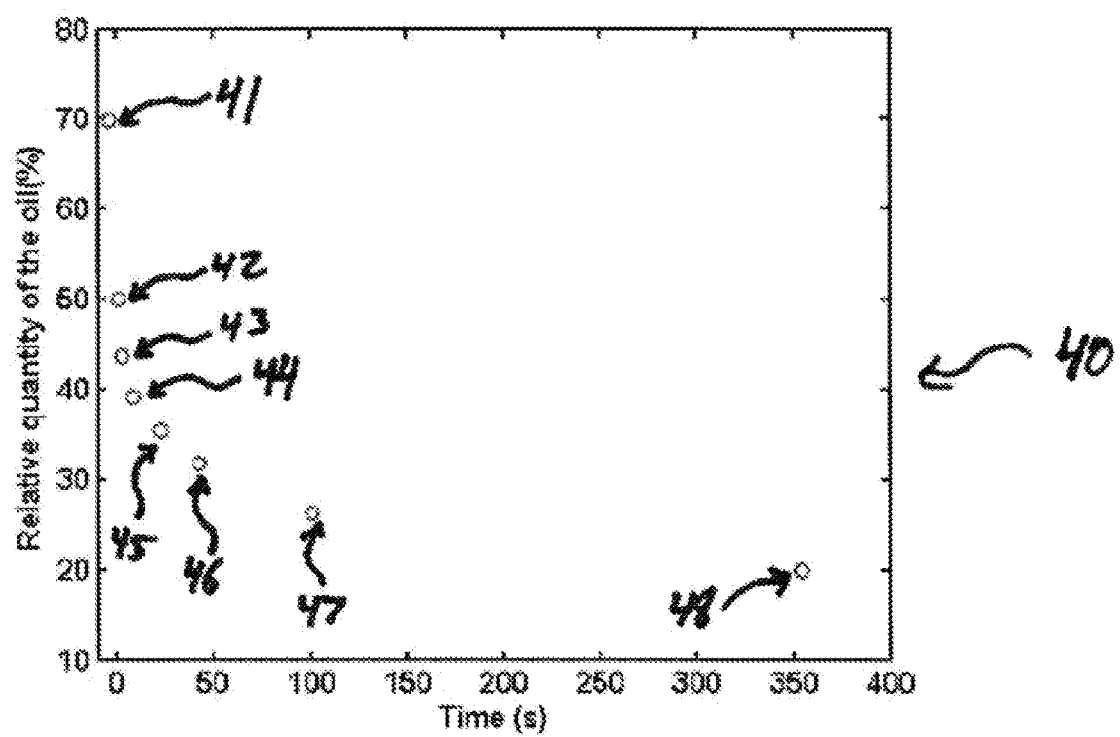
FIG. 4 provides a kinetic plot of the data representing the amount of medium chain triglyceride oil within the pores at set times after the porous grains have been put into contact with the mucin buffer solution from the embodiment shown in FIG. 3.

FIG. 4 provides the kinetic plot 40 for this exemplary embodiment, where each data point corresponds to the plateau height from FIG. 3 at the appropriate measurement time For example, point 41 reflects the plateau height of curve 31 and shows the relative amount of the oil contained in the pores of the SCTAB material. This technique therefore provides a manner for plotting the short term kinetics of liquid release from a porous material. This can have many beneficial applications. In one representative example, one may probe and evaluate the delivery of various flavorants in the mouth upon consumption of certain foods.

In some embodiments of the method, the measurement of the sample's transverse relaxation begins almost immediately after the exposure of the porous material and the at least partially imbibed liquid to the contacting solution. Traditional sample loading into an NMR spectrometer, however, often takes at least 10 seconds if not significantly longer depending on the characteristics of the machine and its operating program. Therefore, information about the initial stages of a chemical reaction or other physicochemical transformation or operation, including the immediate short-term kinetics, cannot be measured using NMR when traditional sample loading is used since there is an inherent delay before measurement after introducing the sample components into cavity of the NMR tube. Thus, in certain embodiments, the porous material and liquid are exposed to the contacting solution in situ inside the NMR probe after the sample is loaded into the NMR spectrometer and the NMR probe is ready to measure the sample's transverse relaxation.

In some embodiments, the porous material and liquid are stored in a first container and the contacting solution is stored in a second container. In certain embodiments, the first and second containers are cylindrical, rectangular, or any other geometric shape. The porous material and liquid are separated from the contacting solution before being exposed to or coming into contact with the contacting solution. In some embodiments, the first and second container share a wall that separates the porous material and liquid from the contacting solution. In certain embodiments, the probe may include moveable structure to permit or initiate exposure between the substances in the first and second containers, such as by moving structure from a first position to a second position. For example, in one embodiment, the wall is lifted up from the sample area to expose the sample components to each other. As another example, in another embodiment, the wall comprises one or more slits or openings that can selectively open up to cause exposure. In certain other embodiments, the first and second container are spatially separated, and exposure may be accomplished by moving one or more of the substances within the probe. In one example embodiment, the porous material and liquid may be injected into the second container, and in another example embodiment, the contacting solution is injected into the first container. In some embodiments, the sample container positioned inside the NMR probe comprises the first container, the second container, or both. In certain exemplary embodiments, the sample container is configured to hold the sample components so that, once loaded into a NMR spectrometer, the sample components are already positioned inside the sample space, i.e. within the probe coil, the area where the generated magnetic field is at its maximum strength, or both. These embodiments advantageously eliminate any relaxation effects or spin polarization artifacts that result from moving sample components from an area experiencing a lower magnetic field strength to the sample space experiencing a relatively higher magnetic field strength as moving even centimeters from the sample space results in a noticeable difference in magnetic field strength. In certain embodiments, at least the portion of the sample container that is positioned inside the NMR probe is cylindrical. In some embodiments the cylinder is approximately 3 mm, 5 mm, 8 mm, 10 mm or 15 mm in diameter. In various embodiments, the cylinder is a standard NMR measurement tube.

In some embodiments, the first container is contained inside the second container, and exposure may be accomplished in a number of different ways. For example, in one embodiment, the first container is then removed to create exposure, in another embodiment, the material is forced outside of the first container into the second container, and in a further embodiment, a combination of such techniques may be used. Further structures and techniques may be used in additional embodiments. These actions may be driven by a wide variety of mechanical components, including but not limited to a piston, a shaft, a holder, or a combination thereof. In some embodiments these components are capable of moving up or down the longitudinal axis of the probe. In some embodiments, the removal or forcing is powered by mechanical power, hydraulic power, pneumatic power, electrical power, human power, or a combination thereof.

In certain embodiments, the exposure is achieved by an exposure mechanism using an actuator that is operably connected to one or more moveable elements. This connection may be direct or indirect, and the moveable elements may be any suitable mechanical component such as those described above. In some embodiments, the actuator moves the one or more moveable elements between a first position and one or more subsequent positions. In certain embodiments, the movement of the moveable part or parts to the second position may permit or initiate the exposure of various sample components such as the porous material, liquid and the contacting solution, such as by removing any separating barriers, driving the components together, driving one or more components into another, or a combination thereof. In some embodiments, when the moveable element or elements are in second position the porous material and liquid are exposed to the contacting solution, the porous material and liquid are driven into the contacting solution, or both. The actuator can be any type known in the art, including but not limited to a lever arm and cable, a screw, a nut, a chain, a rod, a linkage, a linear cam, a rotatable cam, an active material such as a piezoelectric, an electric, pneumatic, or hydraulic actuator, and the like.

In some embodiments, an electric current is applied to a conductor material such that, in the applied magnetic field of the NMR spectrometer, the electric current flowing through the conductor material results in a Lorentz Force acting upon the conductor material. In turn, this force may be used to mechanically move one or more structures within the probe to result in exposure of the porous material and liquid with the contacting solution. This force can be defined by the equation:

$$F = Il \times B$$

where I is the current flowing though the conductor material, l is the length of the conductor material and B is the magnetic field. In certain embodiments, the conductor material is an un-curved wire or is otherwise straight or shaped so that the electric current substantially moves in a single direction and is positioned so that the flow of current I is perpendicular to the direction of the applied magnetic field. Under these conditions, the conductor material will experience a force pushing in a perpendicular direction according to the right hand rule when an electric current is flowing. In some embodiments, the conductor material is shaped and oriented in this way so that, when the electric current is applied, it moves in a particular direction. This movement can be used to achieve exposure of the porous material and liquid with the contacting solution, such as by moving barriers between the substances, forcibly moving one or more of the substances, or a combination thereof. In various example embodiments, the movement of the conductor material may be transferred to initiate or perform the removing of the first or second container, the forcible movement of the porous material and the liquid, the forcible movement of the contacting solution, or a combination thereof. The movement from the Lorentz force can directly or indirectly move various other components including the first container, the second container, the piston, the shaft, a wall separating the first and second containers, or a combination thereof. In one embodiment, the probe may include a moveable actuator connected to the conductor material and operably connected to one or more other components of the probe. The movement of the conductor material may create movement of the actuator, which in turn can move the other component(s) of the probe in the process of creating exposure.

In certain embodiments, the conductor material is a coiled wire or a solenoid coil. When an electric current is applied to the coil the force is defined by the equation:

$$F = I \oint dl \times B.$$

where the variables are defined as before. In these embodiments, the solenoid coil will experience torque when the electric current is applied. In certain embodiments, a solenoid coil is used such that the application of the electric current causes a Lorentzian torque that drives rotation of the coil, and this initiates or performs movement of one or more components of the probe, such as the removal and/or forcing steps described above.

Figure 5:
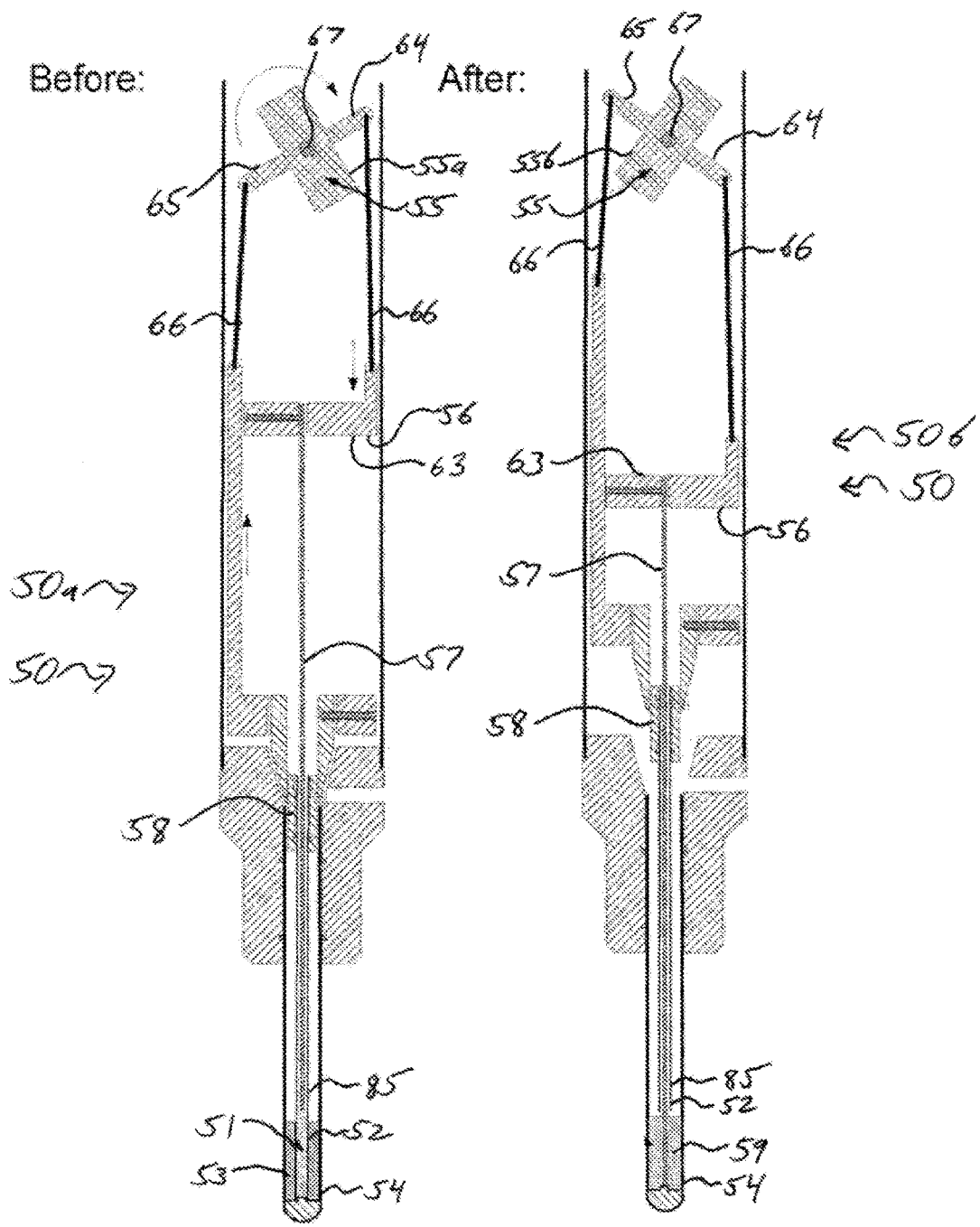
FIG. 5 provides an exemplary embodiment of an apparatus for performing chemical reactions or other physico-chemical transformations or operations in situ inside an NMR probe.

FIG. 5 illustrates an exemplary embodiment of an in situ reaction probe structure 50, where 50a denotes the structure in a first position before initiating exposure to the contacting solution and 50b denotes the structure in a second position after initiating exposure. The probe structure 50 includes an exposure mechanism 63 that can expose at least a first sample component to at least a second sample component inside a sample container within the probe 50. In this exemplary embodiment, the probe 50 includes a first sample component in the form of the porous material and the least partially imbibed liquid 51 inside a first container 52, where in this exemplary embodiment the first container 52 is a first cylindrical tube with a cylindrical wall 85. The wall 85 of the first container 52 functions as a separator to separate the porous material and liquid 51 from a second sample component in the form of the contacting solution 53 in a second container 54, where the second container 54 is a second cylindrical tube that surrounds the first cylindrical tube. In this embodiment, therefore, the second container 54 contains all the sample components and the first container 52 therein. In this exemplary embodiment, the first tube is hermetically sealed from the contents of the second tube, which may be accomplished by using a seal, plug, gasket, or another sealing means or component.

In this exemplary embodiment, the exposure mechanism 63 includes a movable actuator 55 that comprises the conductor material in the form of a solenoid coil and is connected to one or more other moveable components of the exposure mechanism 63, such that movement of the actuator 55 moves one or more other components from a first position to a second position. This movement initiates the exposure. The actuator 55 in this embodiment has a first member 64 coupled to a moveable piston 56 connected to a shaft 57 that is in communication with the first container 52, and a second member 65 that is coupled to a moveable holder 58 that is connected to the wall of the first container 52. As illustrated in FIG. 5, the first and second members 64, 65 may be arms extending from opposite sides of the actuator 55, which are connected to the shaft 57 and the holder 58, respectively, by connectors 66. In this embodiment, the actuator 55 is rotatable or pivotable about an axis of rotation 67, and the first and second members 64, 65 extend generally in opposite directions from the axis 67. It is understood that the solenoid coil or other conductor material may form the entirety or substantial entirety of the actuator 55 in another embodiment.

In the embodiment illustrated in FIG. 5, an electric current is applied to the solenoid coil, causing it to rotate in the clockwise direction, which causes rotational movement of the actuator 55 (from position 55a to 55b). This rotation causes the first member 64 to move downward, which drives the piston 56 to push the shaft 57 axially down into the porous material and the liquid 51, forcing the porous material and the liquid 51 downward. This rotation also simultaneously causes the second member 65 to move upward, which pulls the holder 58 upward, raising the first container 52 and removing the separator between the components 51 and 53. This action results in the creation of a mixture 59 of the porous material, liquid and contacting solution, which can then be probed with the NMR spectrometer. In this embodiment, the mixture 59 is positioned in the second container 54 after exposure, and the second container thereby also forms the sample container for holding the mixture 59 for probing.

In certain embodiments, the components that do not come in contact with the sample and do not come into close proximity of the sample, which can include at least the actuator, solenoid, piston, shaft, or holder depending on the characteristics of the embodiments, are made from a polymer such as caprolon or a metal material such as brass, copper, steel, bronze, or tin. In various embodiments, the components that do come in contact with the sample or come into close proximity of the sample are made of materials that are either substantially or completely free of Hydrogen or other nuclear species that may be probed by NMR or exhibit very short transverse relaxation times so that they do not interfere with the transverse relaxation decays of the liquid of interest. In certain embodiments, "close proximity" is determined as being close enough to overlap with or interfere with the magnetic field generated by the NMR probe coil during pulse sequences or signal measurements. In some embodiments, these components are made of materials that have chemical resistance to one or more commonly used solvents. In certain embodiments, these components are made of glass, quartz glass, Teflon, or a combination thereof. In various embodiments, some or all of these components are a permanent part of the NMR probe and are moveable to allow sample loading, while in others some or all of the components comprise a removeable probe insert.

In accordance with yet another aspect of the invention, a method for performing chemical reactions or other physicochemical operations between two or more components in situ inside a nuclear magnetic resonance probe is provided. In some embodiments, the method comprises loading a sample into a sample container, where a separator separates at least a first sample component of the sample from at least a second component of the sample, placing the sample in a spectrometer, and exposing at least the first sample component to at least the second sample components when the sample is ready for the application of one or more RF pulses or pulse sequences. The wall of the first container 52 in FIG. 5 is one example of such a separator, and other examples are described herein. It is understood that the separator may be formed by further structures that are not described herein and function to separate the components. In certain embodiments, the separator separates three or more sample components from each other before exposure. After the exposure, any type of NMR measurement and analysis may be performed. In certain embodiments, the data acquisition is focused solely on standard spectra and chemical shift data. Other embodiments relate to other known NMR experiments, including but not limited to APT, INEPT, DEPT, NOE, COSY, NOESY, HETCOR, HMQC, HMBC, HETJ, RELAY, DQFCOSY, TQCOSY, TOCSY, INADEQUATE, HOMJ, ROESY, PFG, gCOSY, gDQFCOSY, gHECTOR, gHMQC, or gHMBC. In certain embodiments, the NMR data is analyzed using a Fourier transform or a inverse Laplace transform. In some embodiments, both the first and second sample component are liquids, while in others at least one comprises a solid or a gas.

In certain embodiments, at least the first sample component is exposed to at least the second sample component by lifting a separator from dividing the sample, forcing at least the first sample component into contact with the second sample component, or a combination thereof. In some embodiments this is done by an exposure mechanism, which may comprise an actuator, one or more moveable parts that are configured to move between a first and at least a second position when driven by the actuator. In still other embodiments, the method further comprises applying an electric current to a conductor material such that the conductor material moves or rotates in a particular way due to a Lorentz force. In yet other embodiments, the conductor material is a solenoid coil and the electric current produces a Lorentzian torque that causes the solenoid coil to rotate. In some embodiments, the rotation of the solenoid coil directly or indirectly lifts up the separator while mechanically forcing at least the first sample component into contact with at least the second sample component.

In certain embodiments, the separator is a tube having a first diameter and the sample container is a tube having a second diameter, the second diameter being larger than and concentric with the first diameter. In still other embodiments, the first sample component is forced into contact with at least the second sample component using a shaft moving along a longitudinal axis of the sample container.

These method descriptions are merely exemplary. In certain embodiments, the methods may include additional combinations or substitutions of some or all of the steps described above. Moreover, all aspects, structures, features or components of any of apparatuses of the invention may perform or be included in any appropriate step of the methods. Finally, additional and alternative suitable variations, forms and components for these methods will be recognized by those skilled in the art given the benefit of this disclosure.

Other aspects of the invention relate to apparatuses for performing the inventive methods. In some embodiments, these apparatuses comprise one or more of the structures, features components or combination thereof discussed above in relation to the methods of the invention. Various embodiments combine software and hardware aspects. In some embodiments, these aspects take the form of a computer program product stored by one or more non-transitory computer-readable storage media having computer-readable program code, or instructions, embodied in or on the storage media. The term "computer-readable medium" or "computer-readable storage medium" as used herein includes not only a single medium or single type of medium, but also a combination of one or more media and/or types of media. Such a non-transitory computer-readable medium may store computer-readable instructions (e.g., software) and/or computer-readable data (i.e., information that may or may not be executable). Any suitable computer readable media may be utilized, including various types of tangible and/or non-transitory computer readable storage media such as hard disks, CD-ROMs, optical storage devices, magnetic storage devices, and/or any combination thereof.

In certain embodiments, the apparatuses further comprise one or more non-transitory computer readable media storing computer readable instructions that, when executed by a computer processor, cause the apparatus to perform any of the method steps described above, including but not limited to exposing a porous material and a liquid to a contacting solution, applying an electrical current to a conductor material, applying one or more radiofrequency pulses or pulse sequences, measuring one or more transverse relaxations of the sample, performing an inverse Laplace transformation using the computer processor on the transverse relaxations to determine amount of the liquid contained inside the porous material and an amount of the liquid outside the porous material, waiting a predetermined time period between pulses or pulse sequences, comparing or plotting various amounts of in-pore and out-of-pore liquid, activating an exposure mechanism, activating an actuator, lifting a separator, forcing a sample component, removing a container, or a combination thereof.

Figure 12:
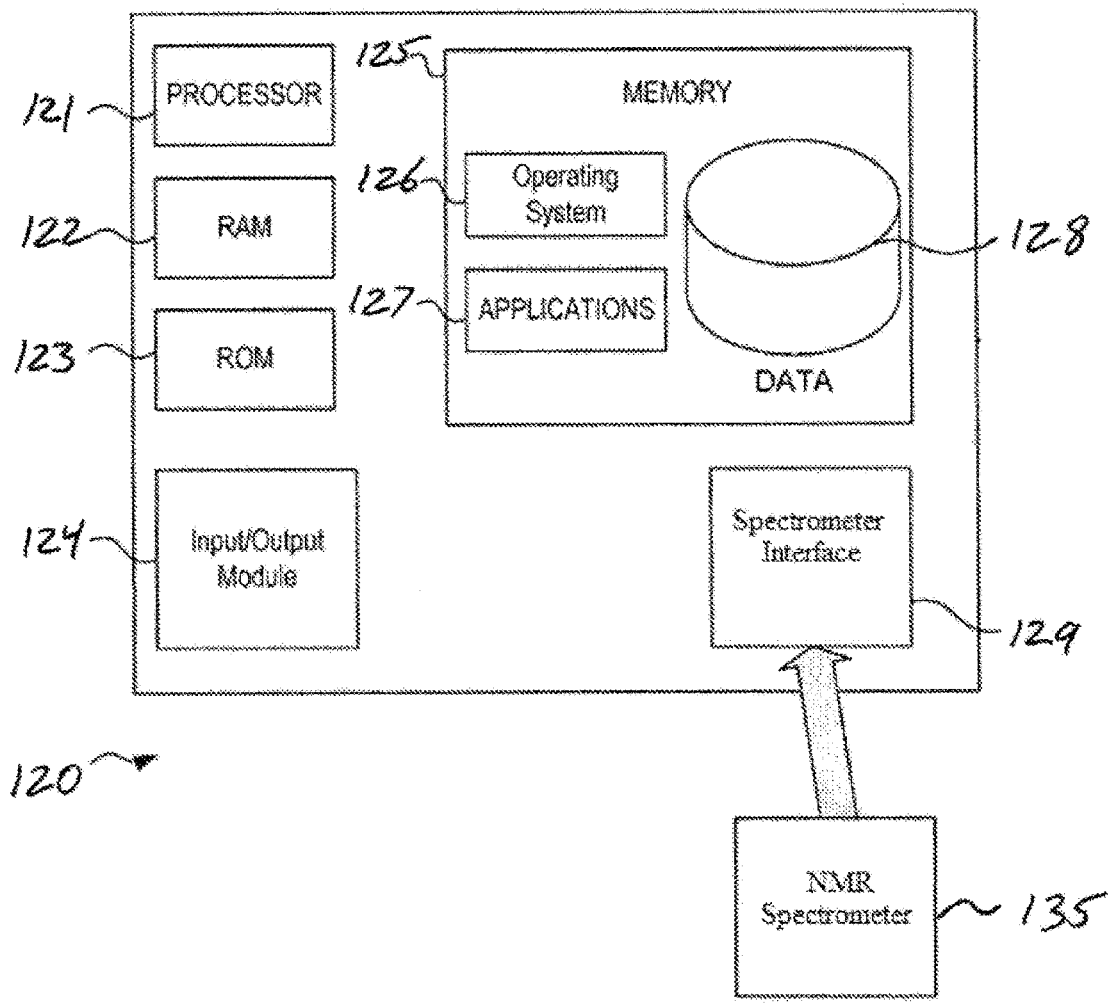
FIG. 12 provides a block diagram of an exemplary computing device that may be used with certain aspects of this disclosure.

As noted above, some aspects of the embodiments disclosed herein may be executed by one or more processors on a computing device. Such processors may execute computer-executable instructions stored on non-transitory computer-readable media. FIG. 12 illustrates a block diagram of a generic computing device 120 that may be used according to an illustrative embodiment of the disclosure. The computing device 120 may have a processor 121 for controlling overall operation of the device and its associated components, including RAM 122, ROM 123, input/output module 124, and memory 125. Input/Output (I/O) 124 may include a microphone, keypad, touch screen, camera, and/or stylus through which a user of computing device 120 may provide input, and may also include one or more of a speaker for providing audio output and a video display device for providing textual, audiovisual and/or graphical output. Other I/O devices through which a user and/or other device may provide input to the computing device 120 also may be included.

Figure 13:
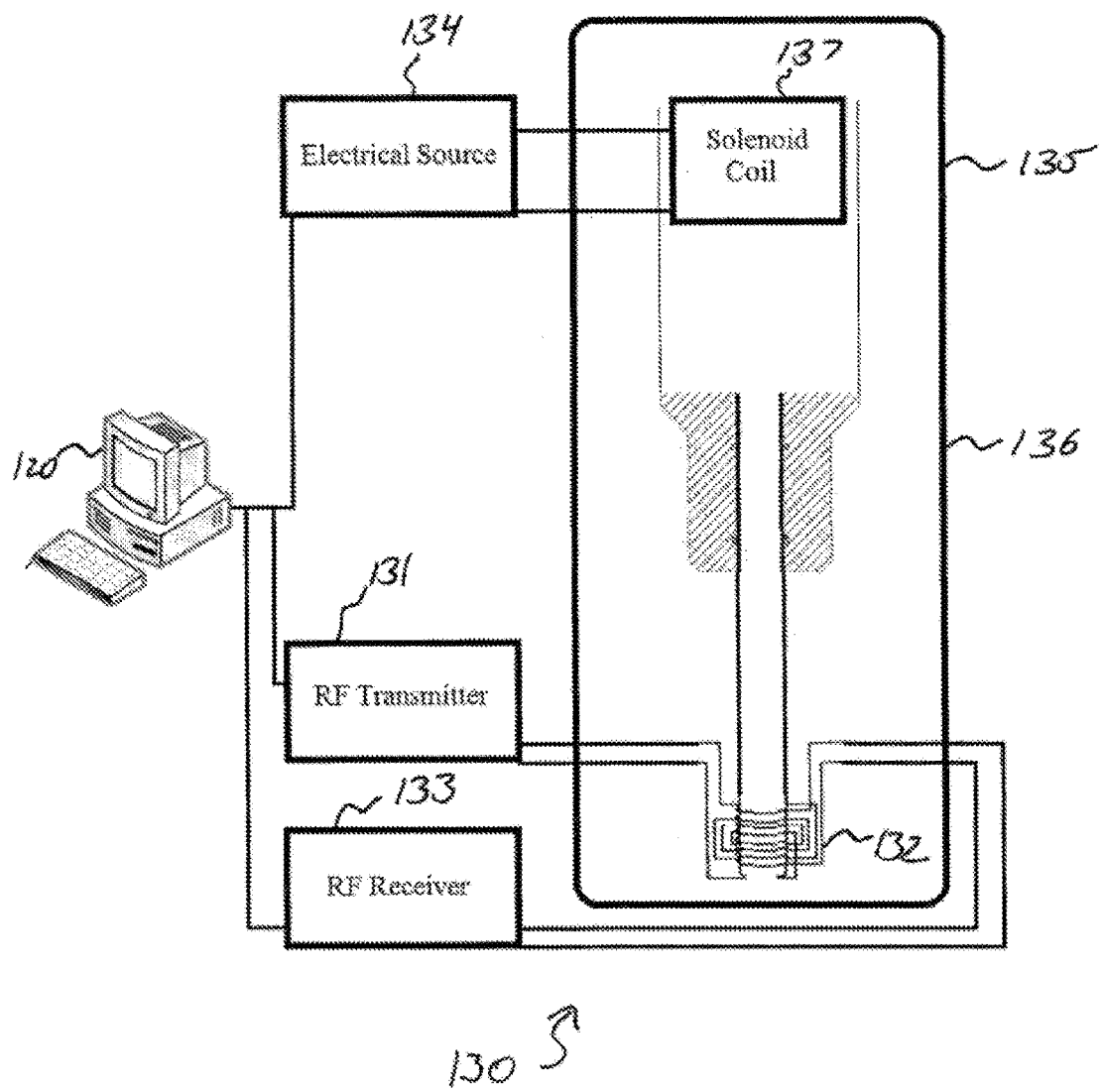
FIG. 13 provides an illustrative diagram of an exemplary embodiment of a computer operated NMR measurement apparatus.

Software may be stored within memory 125 and/or storage to provide instructions to processor 121 for enabling computing device 120 to perform various functions. For example, memory 125 may store software used by the computing device 120, such as an operating system 126, application programs 127, and an associated database 128. The computing device 120 is connected to the NMR Spectrometer 130 through a spectrometer interface 129. In some embodiments the application programs 127 may include NMR operation programs or data interpretation programs capable of analyzing the measured NMR signals, including programs capable of performing Fourier transformations, Laplace transformations, or inverse Laplace transformations. FIG. 13 provides a simplified block diagram of an exemplary embodiment of a computer operated NMR measurement apparatus 130 (please note the portions of the figure not shown in block form are illustrative only and are explicitly not drawn to scale). In this embodiment, the computing device 120 is connected via the spectrometer interface 129 (not shown) to various components of the NMR spectrometer 135, including the RF transmitter 131, the RF receiver 133, and the electrical source 134, where the NMR spectrometer comprises a probe coil 132 and a magnet 136. The computer operated NMR measurement apparatus 130 may include other standard components, including but not limited to sample changers, lock transmitters, lock receiver, temperature regulation, amplifiers, shim regulation components or gradient control/amplifier components. In some embodiments, the NMR magnet has a field strength of approximately 11.7 Tesla, while in others it ranges from approximately 1.41 Tesla to approximately 23.5 Tesla. In certain embodiments, the NMR magnet has a field strength of approximately 2.35 Tesla, 4.7 Tesla, 7.05 Tesla, 14.1 Tesla, 18.8 Tesla, 21.1 Tesla, or 23.5 Tesla.

In this exemplary embodiment, when the computer processor 121 (not shown) executes certain computer-executable instructions stored on non-transitory computer-readable media, the computing device 120 causes the RF transmitter 131 to send a RF pulse or pulse sequence to the sample via the probe coil 132, and then the RF receiver 133 measures the received NMR signals from the probe coil 132. In this exemplary embodiment, the computing device 120 also causes the electrical source 134 to send an electrical current though the solenoid coil 137, where this may occur before or after the RF pulse or pulse sequence is applied to the sample. In other embodiments, the computing device 120 is directly or indirectly connected to another type of actuator as described above. In certain other embodiments, no actuator, solenoid coil or the like components for performing in situ reactions are present.

These descriptions of the apparatuses are merely exemplary. In certain embodiments, the apparatuses comprise additional combinations or substitutions of some or all of the components described above in relation to any of the disclosed methods or apparatuses. Moreover, additional and alternative suitable variations, forms and components for the apparatuses will be recognized by those skilled in the art given the benefit of this disclosure.

All of the above described method and apparatus descriptions for various aspects of the invention are representative. In certain embodiments, a method or apparatus may include additional combinations or substitutions of some or all of the steps and/or components described herein or their equivalents. Moreover, additional and alternative suitable variations, forms and components will be recognized by those skilled in the art given the benefit of this disclosure.

EXAMPLES

The above inventive methods and apparatuses were investigated by a series of exemplary experiments. All of the representative experiments discussed herein were performed by a $^1$H NMR in a Bruker Avance 500 NMR spectrometer with a resonance frequency of 500.13 MHz. A CPMG pulse sequence was applied in each of these experiments. As noted above CPMG experiments can be performed with different pulse spacing times. The pulse spacing values used were the below noted values where there was no significant prolongation of the signal decays. This was tested by recording transverse relaxation decays with different pulse spacing in the CPMG sequence for every sample. The comparison of those decays provided an indication of the threshold pulse spacing value below which there were no significant artifacts.

Example 1

Figure 6:
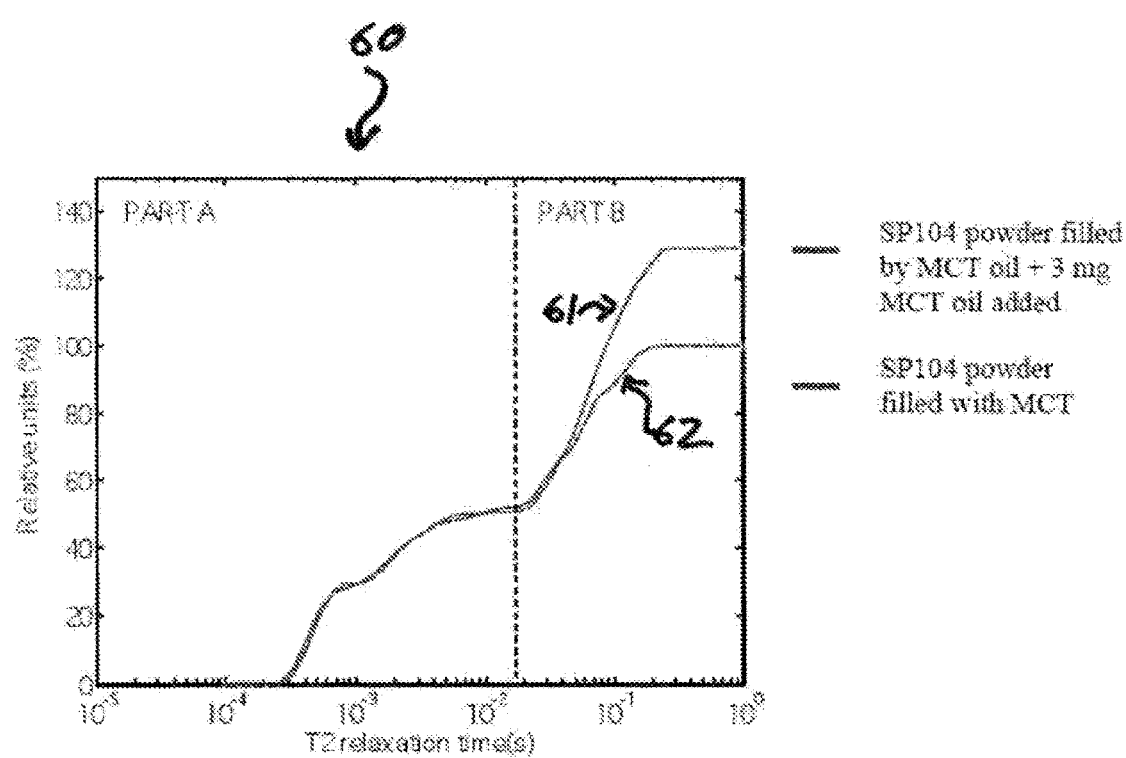
FIG. 6 provides an exemplary plot showing the relative transverse relaxation proportions of a control sample and a sample with additional out-of-pore liquid.

Two samples of SP104 powder were loaded (imbibed) with an equivalent amount of medium chain triglyceride oil. In one sample, an additional 3 mg of the oil was then added to the sample. FIG. 6 provides the plot 60 of the measurement of the transverse relaxation distribution of each sample after performance of the inverse Laplace transformation. Curve 61 shows the data for the sample with the additional oil added and curve 62 shows the data for the sample without the additional oil. The portion of the curves below the plateau signifying the amount of in-pore oil are equivalent, while the signal for out-of-pore oil is much larger for curve 61 illustrating the sample with additional oil added. This clearly shows the portion of the curve after the plateau reflects the relative amount of out-of-pore material that exhibits a longer transverse relaxation time.

Example 2

Figure 7:
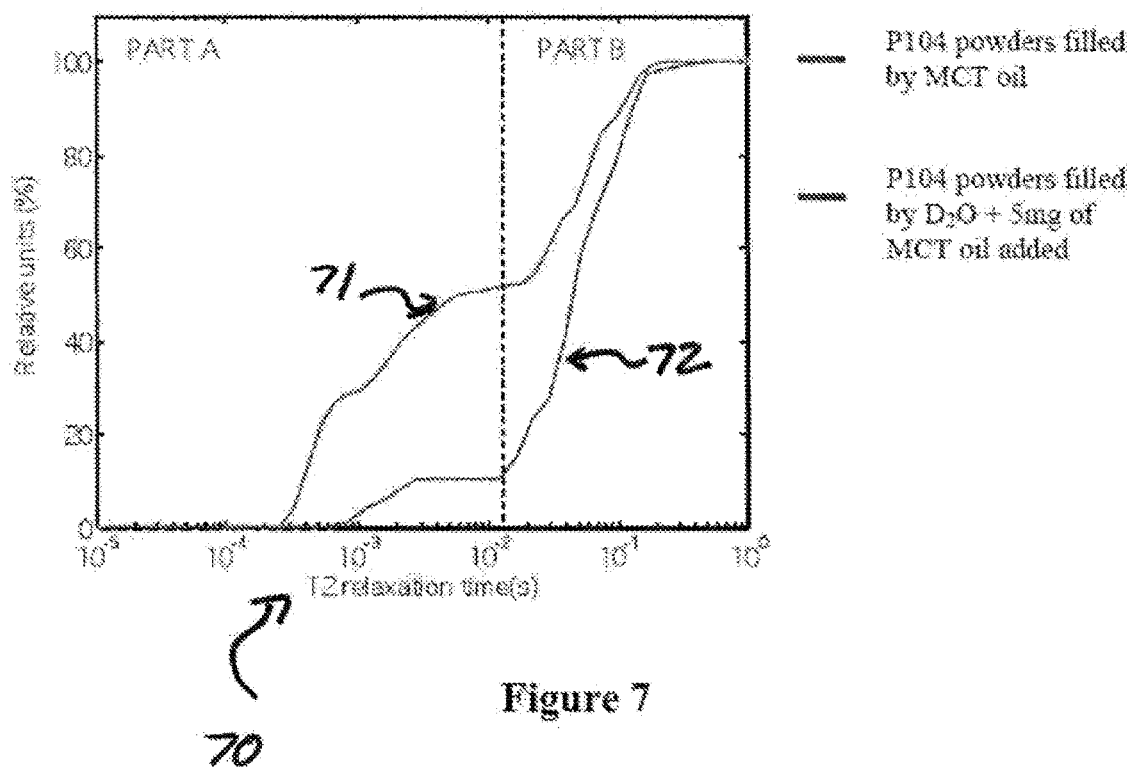
FIG. 7 provides an exemplary plot showing the relative transverse relaxation proportions of a control sample and a sample with additional in-pore liquid.

One sample of P104 powder was filled with medium chain triglyceride oil. A second was filled with heavy water and then 5 mg of the same oil was subsequently added. FIG. 7 provides the plot 70 of the measurement of the transverse relaxation distribution of each sample after performance of the inverse Laplace transformation. Curve 71 shows the data for the sample with just the oil and curve 72 shows the data for the sample initially loaded with heavy water. The portion of curve 72 before the plateau is minimal, clearly showing the portion of the curve before the plateau reflects in-pore material with a shorter transverse relaxation time.

Example 3—Long Term Steady State

Twenty samples were prepared to examine the long term steady state reached 24 hours after a liquid and porous material combination were added into an aqueous contacting solution. These tests were performed with a DIFF30 diffusion probe equipped with a 5 mm $^1$H radiofrequency insert. A 7.5 microsecond length 90 degree pulse was used. All spectrometer shims were set to zero and the magnetic field was calibrated to zero frequency offset. Samples of porous powders with a weight of 30-40 mg were placed in a 5 mm NMR tube. Several transverse relaxation curves were recorded to improve the signal to noise ratio. Table 1 illustrates the results comparing the initial and 24 hours of in-pore and out-of-pore ratios. After twenty four hours, all in-pore material has settled to the bottom of the sample as sediment, and the fraction of oil released into the solution from the buffer was at the top of the sample. Data for the following samples was taken:

Sample 1: SP104 porous material was loaded with medium chain triglyceride oil ("MCT") and released into a mucin buffer;
Sample 2: SP104 porous material was loaded with MCT and released into an electrolyte buffer without mucin;
Sample 3: SP104 porous material was loaded with sunflower oil ("SF") and released into a mucin buffer;
Sample 4: SP104 porous material was loaded with SF and released into an electrolyte buffer without mucin;
Sample 5: SP104 porous material was loaded with propylene glycol ("PG") and released into a mucin buffer;
Sample 6: SP104 porous material was loaded with PG and released into an electrolyte buffer without mucin;
Sample 7: SP104 porous material was loaded with glycerine and released into a mucin buffer;
Sample 8: SP104 porous material was loaded with glycerine and released into an electrolyte buffer without mucin;
Sample 9: SCTAB porous material was loaded with MCT and released into a mucin buffer;
Sample 10: SCTAB porous material was loaded with MCT and released into an electrolyte buffer without mucin;
Sample 11: SCTAB porous material was loaded with SF and released into a mucin buffer;
Sample 12: SCTAB porous material was loaded with SF and released into an electrolyte buffer without mucin;
Sample 13: SCTAB porous material was loaded with PG and released into a mucin buffer;
Sample 14: SCTAB porous material was loaded with PG and released into an electrolyte buffer without mucin;
Sample 15: SCTAB porous material was loaded with glycerine and released into a mucin buffer;
Sample 16: SCTAB porous material was loaded with glycerine and released into an electrolyte buffer without mucin;
Sample 17: SP104 porous material was loaded with MCT and meat flavor, and then released into a mucin buffer;
Sample 18: SP104 porous material was loaded with MCT and meat flavor, and then released into an electrolyte buffer without mucin;
Sample 19: SP104 porous material was loaded with PG and meat flavor, and then released into a mucin buffer; and Sample 20: SP104 porous material was loaded with PG and meat flavor, and then released into an electrolyte buffer without mucin.

TABLE 1

| Sample No. | Fraction of in-pore Oil (% ± 0.5%) | | Fraction of out-of-pore Oil (% ± 0.5%) | | Fraction of Oil |
|---|---|---|---|---|---|
| | Initial State | After Release in Solution | Initial State | After Release in Solution (in sediment) | Released to Solution [%] |
| 1  | 62.0 | 52.0 | 38.0 | 12.0 | 36.0 |
| 2  | 62.0 | 52.5 | 38.0 | 12.5 | 35.0 |
| 3  | 68.0 | 14.0 | 32.0 | 52.0 | 34.0 |
| 4  | 68.0 | 14.5 | 32.0 | 60.5 | 25.0 |
| 5  | 74.0 | 63.5 | 26.0 | 24.5 | 12.0 |
| 6  | 74.0 | 65.0 | 26.0 | 35.0 | 0.0 |
| 7  | 65.0 | 31.0 | 35.0 | 58.0 | 11.0 |
| 8  | 65.0 | 32.0 | 35.0 | 57.0 | 11.0 |
| 9  | 61.5 | 52.5 | 38.5 | 10.5 | 37.0 |
| 10 | 61.5 | 51.5 | 38.5 | 31.5 | 17.0 |
| 11 | 69.0 | 3.0  | 31.0 | 17.0 | 80.0 |
| 12 | 69.0 | 7.5  | 31.0 | 12.5 | 80.0 |
| 13 | 55.0 | 1.5  | 45.0 | 11.5 | 87.0 |
| 14 | 55.0 | 2.0  | 45.0 | 7.0  | 91.0 |
| 15 | 74.5 | 1.5  | 25.5 | 11.5 | 87.0 |
| 16 | 74.5 | 1.5  | 25.5 | 9.5  | 89.0 |
| 17 | 80.0 | 1.0  | 20.0 | 16.0 | 83.0 |
| 18 | 80.0 | 1.5  | 20.0 | 14.5 | 84.0 |
| 19 | 76.0 | 4.5  | 24.0 | 13.0 | 82.5 |
| 20 | 76.0 | 6.0  | 24.0 | 14.0 | 80.0 |

For the samples with glycerine or propylene glycol, these liquids solubilized in the buffer solutions. Thus, almost all the liquid is released from the pores and goes into the aqueous phase—any remaining liquid in the pores after 24 hours is the faction that is dissolved in the solution filling the pores.

Example 4—Release Kinetics

Ten samples were prepared to examine the release kinetics of a liquid from a porous material once added into an aqueous contacting solution. These tests were performed at 500 MHz $^1$H frequency with a DIFF30 diffusion probe equipped with 10 mm $^1$H radiofrequency inserts. A 11.5 microsecond length 90 degree pulse was used. All spectrometer shims were set to zero and the magnetic field calibrated to zero frequency offset. Liquid loaded powders with a weight of 58-63 mg were placed into an inner tube (similar to tube 52 in FIG. 5) and the space between the inner tube and outer tube (similar to tube 54 in FIG. 5) was filled with 0.3 mL of a contacting solution. The pulse delays of the CPMG experiment were set based on the results of the corresponding long term steady state experiments. Several transverse relaxation curves were recorded to improve the signal to noise ratio. Data for the following samples was taken:

Sample 1: SP104 porous material was loaded with MCT and released into a mucin buffer, where the CPMG sequence utilized a 155 microsecond pulse delay;

Sample 2: SP104 porous material was loaded with SF and released into a mucin buffer, where the CPMG sequence utilized a 155 microsecond pulse delay;

Sample 3: SP104 porous material was loaded with PG and released into a mucin buffer, where the CPMG sequence utilized a 155 microsecond pulse delay; and Sample 4: SP104 porous material was loaded with Glycerine and released into a mucin buffer, where the CPMG sequence utilized a 155 microsecond pulse delay.

Figure 8:
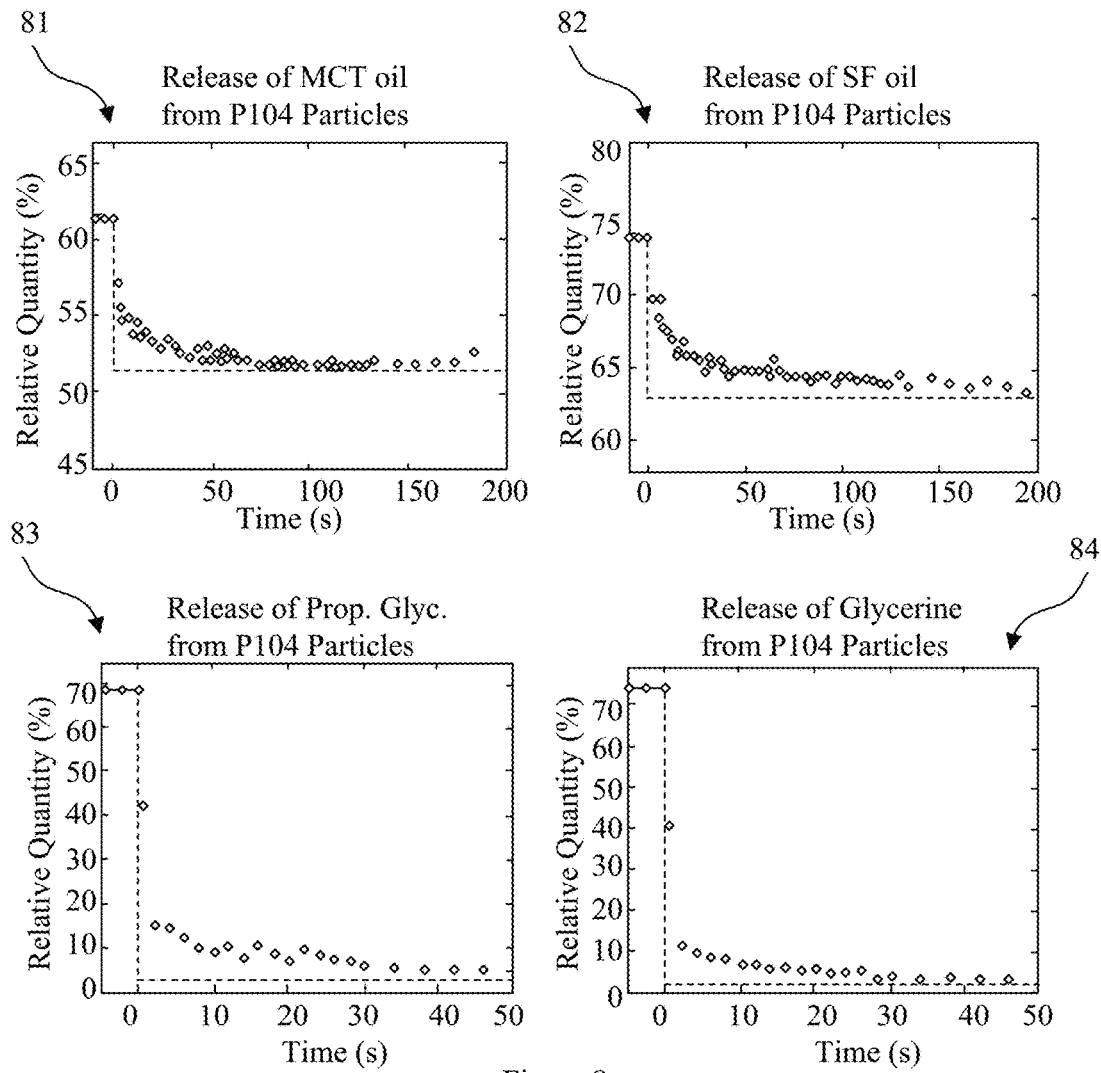
FIG. 8 provides plots showing the release kinetics data of various liquids from SP104 porous material.

The kinetic plots from samples 1-4 are provided in FIG. 8, where plot 81 shows the kinetic data for sample 1, 82 the plot for sample 2, 83 for sample 3, and 84 for sample 4.

Sample 5: SCTAB porous material was loaded with MCT and released into a mucin buffer, where the CPMG sequence utilized a 55 microsecond pulse delay;

Sample 6: SCTAB porous material was loaded with SF and released into a mucin buffer, where the CPMG sequence utilized a 55 microsecond pulse delay;

Sample 7: SCTAB porous material was loaded with PG and released into a mucin buffer, where the CPMG sequence utilized a 55 microsecond pulse delay; and Sample 8: SCTAB porous material was loaded with Glycerine and released into a mucin buffer, where the CPMG sequence utilized a 55 microsecond pulse delay.

Figure 9:
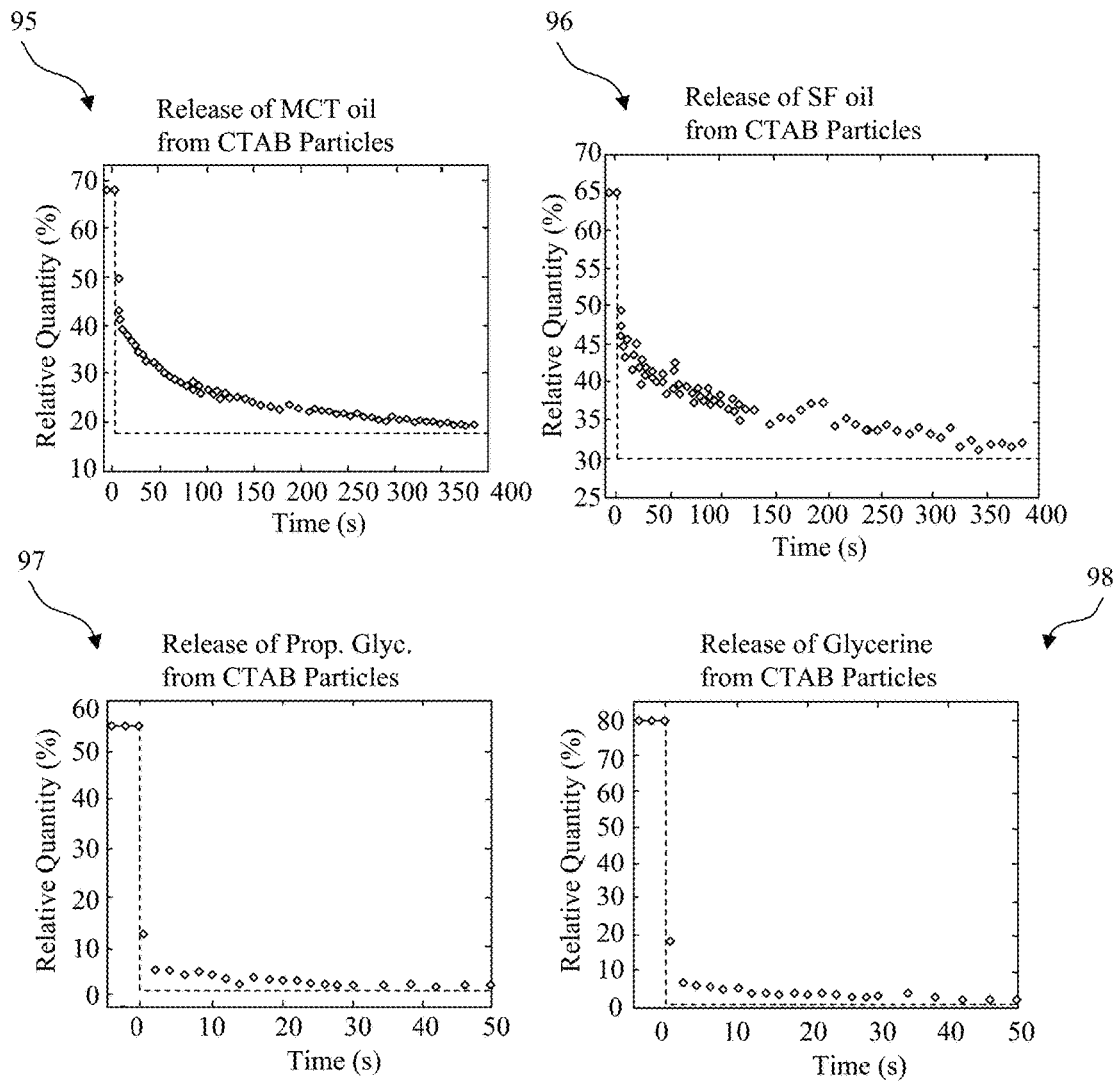
FIG. 9 provides plots showing the release kinetics data of various liquids from SCTAB porous material.

The kinetic plots from samples 5-8 are provided in FIG. 9, where plot 95 shows the kinetic data for sample 5, 96 the plot for sample 6, 97 for sample 7, and 98 for sample 8.

Sample 9: SP104 porous material was loaded with SF and released into a Deuterated Chloroform buffer, where the CPMG sequence utilized a 255 microsecond pulse delay.

Sample 10: Re-dried powder from sample 9 released into an electrolyte buffer without mucin buffer, where the CPMG utilized a 255 microsecond pulse delay.

Figure 10:
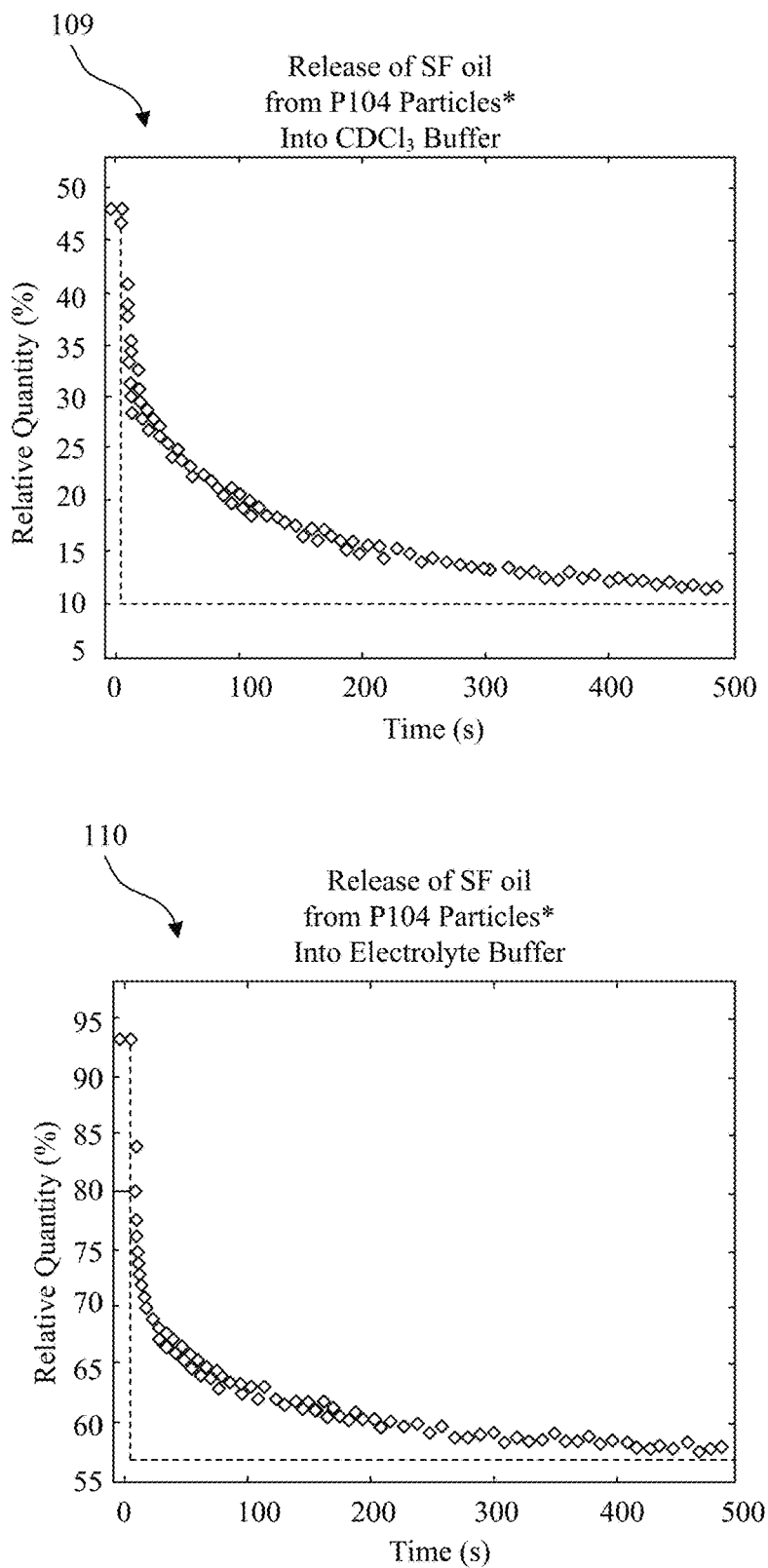
FIG. 10 provides plots showing the release kinetics data of sunflower oil from SP104 porous material for an initial sample and a re-dried sample prepared from the same material.

The kinetic plots from samples 9 and 10 are provided in FIG. 10, where plot 109 shows the kinetic data for sample 9, and plot 110 shows the data for sample 10.

When comparing the plots in FIG. 10 it is important to recall the amount of SF oil is constant. When the solvent was evaporated most of the oil (over 90%) resided in-pore compared to a much smaller number (just over 50%) previously, where presumably some of this oil was stuck on the outside surface of the powder. This type of experiment can be used to determining the filling capabilities of a certain systems and/or material by capillary action.

All kinetic curves were fitted using a Levenberg-Marquardt least-squares fitting algorithm to a model of the same of two exponential function with five unlocked fitting parameters. The parameters were:

$I_0$—initial amplitude, the percentage of in-pore oil in the initial state. Approximate error is ±2%;

P—relative proportion of the faster of the two transverse decays. The proportion of the slower decay is 1−P;

$I_{long}$—the long-time baseline, the percentage of in-pore oil in the long-time (~1000 second) limit (note this parameter is not the same as that obtained after 24 hours and presented in Table 1). Approximate error is ±2%;

$\tau_{fast}$ and $\tau_{slow}$—the two time constants.

TABLE 2

| Sample No. | Initial Amount of in-pore Oil $I_o$ [%] | Oil Remaining in-pro $I_{long}$ [%] | $\tau_{fast}$ [s] | $\tau_{slow}$ [s] | Release Time for Half of the in-pore Oil [s] | Relative Proportion of the fast decay P |
|---|---|---|---|---|---|---|
| 1 | 61 | 51 | 2.4 | 34* | 2.3 | 0.69 |
| 2 | 73 | 63 | 6   | 84  | 6   | 0.73 |

TABLE 2-continued

| Sample No. | Initial Amount of in-pore Oil $I_o$ [%] | Oil Remaining in-pro $I_{long}$ [%] | $\tau_{fast}$ [s] | $\tau_{slow}$ [s] | Release Time for Half of the in-pore Oil [s] | Relative Proportion of the fast decay P |
|---|---|---|---|---|---|---|
| 3 | 69 | 4.5 | 0.14 | 16 | 0.13 | 0.80 |
| 4 | 75 | 1 | 0.14 | 23 | 0.11 | 0.88 |
| 5 | 68 | 20 | 0.5 | 78 | 0.9 | 0.57 |
| 6 | 65 | 33 | 0.12* | 95 | 0.2* | 0.61 |
| 7 | 55 | 1 | 0.06 | 80* | 0.04 | 0.95 |
| 8 | 80 | 0 | 0.05 | 67 | 0.04 | 0.92 |
| 9 | 50 | 12 | 3.5 | 103 | 13 | 0.47 |
| 10 | 88 | 58 | 3 | 85 | 5 | 0.56 |

*parameters with large inaccuracy.

Figure 11:
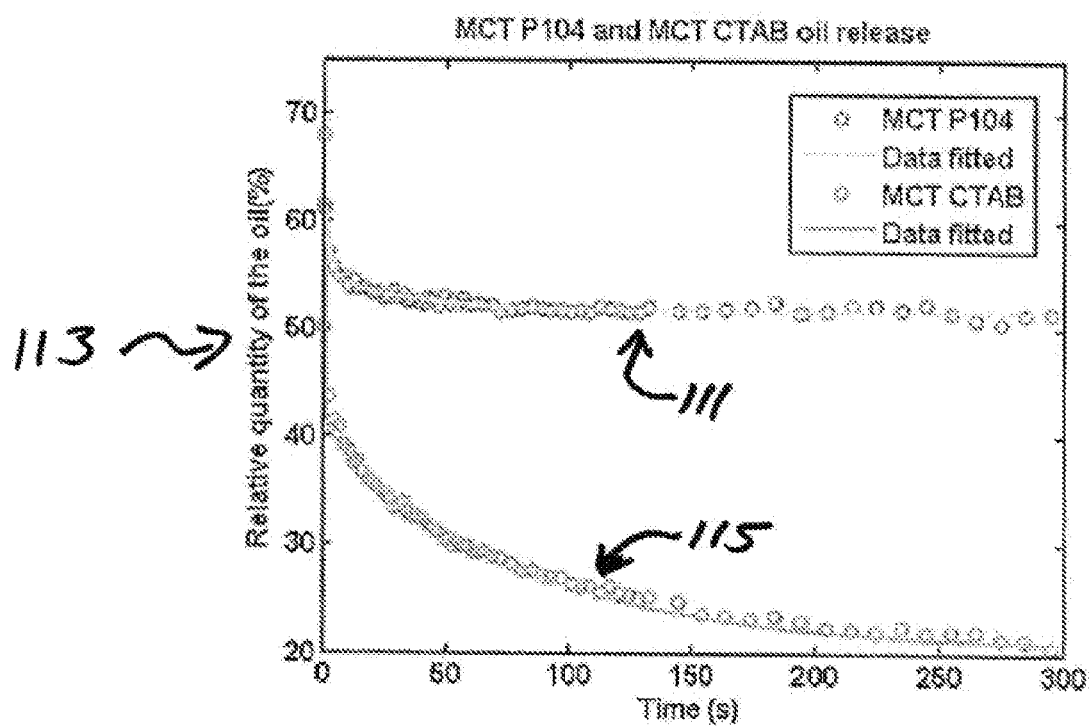
FIG. 11 provides a plot showing the relative release kinetics data of medium chain triglyceride from different porous materials.

Comparing the fitted curves and/or the raw kinetic data allows comparison of the release behavior and kinetics of different materials. As a representative example, FIG. 11 provides a plot 113 where the two curves 111 and 115 show the fitted curve for the kinetic data of samples 1 and 5, respectively, clearly illustrating the difference in release kinetics and the faster delivery of MCT from the SCTAB porous material compared to SP104, despite having an initially higher amount of in-pore MCT (68% in-pore initially for SCTAB compared to 61% in-pore for the SP104 material).

What is claimed is:

1. An apparatus for performing chemical reactions in situ inside a nuclear magnetic resonance probe, the apparatus comprising:
a sample container;
a separator that separates at least a first sample component of a sample from at least a second sample component of the sample inside the sample container; and
an exposure mechanism comprising an actuator operably connected to at least a first moveable element, wherein the actuator is configured to move the first moveable element between at least a first position and a second position, and wherein the first sample component is separated from the second sample component when the first moveable element is in the first position and the first sample component is exposed to the second sample component inside the sample container when the first moveable element is in the second position;
wherein the exposure mechanism can be selectively activated to expose at least the first sample component to at least the second sample component inside the sample container at any time after the components are loaded, including when the sample is loaded into a nuclear magnetic resonance spectrometer such that it is ready for the application of a radiofrequency pulse or pulse sequence by a nuclear magnetic resonance probe; and
wherein the sample components, when the sample container is loaded into the nuclear magnetic resonance spectrometer, are positioned within a sample space encircled by a probe coil of the nuclear magnetic resonance probe.

2. The apparatus of claim 1, wherein the actuator is operably connected to at least a second moveable element and the actuator is configured to move the second moveable element between at least a first position and a second position, and wherein the first sample component is separated from the second sample component when the second moveable element is in the first position and the first sample component is exposed to the second sample component inside the sample container when the second moveable element is in the second position.

3. The apparatus of claim 1, wherein the moveable element comprises the separator, wherein the separator separates the first sample component and the second sample component when the moveable element is in the first position, and wherein the first sample component is exposed to the second sample component when the moveable element is in the second position.

4. The apparatus of claim 1, wherein the moveable element is configured to move the first sample component to initiate exposure of the first sample component and the second sample component when the moveable element moved from the first position to the second position.

5. The apparatus of claim 1, wherein the exposure mechanism is configured to lift the separator from the sample, force the first sample component into contact with the second sample component, or a combination thereof when activated.

6. The apparatus of claim 5, the exposure mechanism further comprising an electrical source and the actuator comprises a conductor material electrically connected to the electrical source, wherein the actuator is mounted such that it is configured to move or rotate in a particular way due to a Lorentz force when an electrical current is supplied by the electrical source to the conductor material and the conductor material is in the presence of a magnetic field.

7. The apparatus of claim 6, wherein the conductor material is a solenoid coil and the electric current produces a Lorentzian torque that causes the solenoid coil to rotate.

8. The apparatus of claim 7, wherein the rotation of the solenoid coil is configured to lift up the separator while mechanically forcing at least the first sample component into contact with at least the second sample component.

9. The apparatus of claim 1, wherein the separator is a tube having a first diameter, the sample container is a tube having a second diameter, the second diameter being larger than the first diameter.

10. The apparatus of claim 1, wherein the moveable element comprises a shaft capable of moving at least the first sample component along a longitudinal axis of the apparatus such that it is configured to drive the first sample component into contact with the second sample component when the moveable element moved from the first position to the second position.

11. A method for performing chemical reactions in situ inside a nuclear magnetic resonance probe, the method comprising:
loading a sample into a sample container, wherein a separator separates at least a first sample component of the sample from at least a second sample component of the sample inside the sample container;

placing the sample into a nuclear magnetic resonance spectrometer, wherein the sample components, once the sample is placed into the nuclear magnetic resonance spectrometer, are positioned within a sample space encircled by a probe coil of a nuclear magnetic resonance probe;

exposing at least the first sample component to at least the second sample component inside the sample container when the sample is ready for the application of a radiofrequency pulse or pulse sequence by the nuclear magnetic resonance probe.

12. The method of claim 11, wherein at least the first sample component is exposed to at least the second sample component by lifting the separator from the sample, forcing at least the first sample component into contact with the second sample component, or a combination thereof.

13. The method of claim 12, further comprising applying an electrical current to a conductor material such that the conductor material moves or rotates in a particular way due to a Lorentz force.

14. The method of claim 12, wherein the conductor material is a solenoid coil and the electric current produces a Lorentzian torque that causes the solenoid coil to rotate.

15. The method of claim 14, wherein the rotation of the solenoid coil lifts up the separator while mechanically forcing at least the first sample component into contact with at least the second sample component.

16. The method of claim 11, wherein the separator is a tube having a first diameter, the sample container is a tube having a second diameter, the second diameter being larger than the first diameter.

17. The method of claim 11, further comprising forcing at least the first sample component into contact with at least the second sample component using a shaft moving along a longitudinal axis of the sample container.

18. An apparatus for performing chemical reactions in situ inside a nuclear magnetic resonance probe, the apparatus comprising:

a sample container;

a separator that separates at least a first sample component of a sample from at least a second sample component of the sample inside the sample container, wherein at least one sample component comprises a solid material, and wherein the sample components, when the sample container is loaded into a nuclear magnetic resonance spectrometer, are positioned within a sample space encircled by a probe coil of the nuclear magnetic resonance probe;

one or more non-transitory computer readable media storing computer readable instructions that, when executed by a computer processor, cause the apparatus to:

activate an exposure mechanism to expose at least the first sample component to at least the second sample component inside the sample container;

apply a first radiofrequency pulse or pulse sequence to the sample; and measure the sample's magnetic resonance signals;

wherein the exposure mechanism comprises an actuator operably connected to at least a first moveable element, wherein the actuator is configured to move the first moveable element between at least a first position and a second position, and wherein the first sample component is separated from the second sample component when the first moveable element is in the first position and the first sample component is exposed to the second sample component inside the sample container when the first moveable element is in the second position.

19. The apparatus of claim 18, wherein the instructions are configured to cause the exposure mechanism to lift a separator from the sample, force at least the first sample component into contact with the second sample component, or a combination thereof when activated.

20. The apparatus of claim 19, wherein the exposure mechanism further comprises an electrical source and a conductor material electrically connected to the electrical source, the conductor material is directly or indirectly connected to the separator, and the conductor material is mounted such that it will move or rotate in a particular way due to a Lorentz force when an electrical current is supplied by the electrical source to the conductor material and the conductor material is in the presence of a magnetic field.

* * * * *